United States Patent
Sekine et al.

(10) Patent No.: US 10,031,128 B2
(45) Date of Patent: Jul. 24, 2018

(54) SCREENING METHOD, SCREENING KIT AND ANALYSIS PROGRAM

(71) Applicant: National Institutes for Quantum and Radiological Science and Technology, Chiba-shi, Chiba (JP)

(72) Inventors: Emiko Sekine, Chiba (JP); Takashi Shimokawa, Chiba (JP); Megumi Ueno, Chiba (JP); Etsuko Nakamura, Chiba (JP); Miyako Nakawatari, Chiba (JP); Takeshi Murakami, Chiba (JP); Takashi Imai, Chiba (JP); Kazunori Anzai, Chiba (JP); Kenichiro Matsumoto, Chiba (JP); Ikuo Nakanishi, Chiba (JP)

(73) Assignee: NATIONAL INSTITUTES FOR QUANTUM AND RADIOLOGICAL SCIENCE AND TECHNOLOGY, Chiba-shi (JP)

( * ) Notice: Subject to any disclaimer, the term of this patent is extended or adjusted under 35 U.S.C. 154(b) by 199 days.

(21) Appl. No.: 14/388,346

(22) PCT Filed: Mar. 26, 2013

(86) PCT No.: PCT/JP2013/002032
§ 371 (c)(1),
(2) Date: Sep. 26, 2014

(87) PCT Pub. No.: WO2013/145708
PCT Pub. Date: Oct. 3, 2013

(65) Prior Publication Data
US 2015/0212067 A1    Jul. 30, 2015

(30) Foreign Application Priority Data

Mar. 27, 2012    (JP) .................. 2012-072619

(51) Int. Cl.
*G01N 33/50*    (2006.01)
*C12N 13/00*    (2006.01)

(52) U.S. Cl.
CPC ......... *G01N 33/5014* (2013.01); *C12N 13/00* (2013.01); *G01N 33/5026* (2013.01); *G01N 33/5044* (2013.01); *G01N 33/5047* (2013.01); *G01N 2800/40* (2013.01)

(58) Field of Classification Search
None
See application file for complete search history.

(56) References Cited

U.S. PATENT DOCUMENTS

2003/0087331 A1* 5/2003 Pettit .................. G01N 33/5008
435/29

OTHER PUBLICATIONS

E Bordon, LAH Hernandez, PC Lara, B Pinar, F Fontes, CR Gallego, M Lloret. Prediction of clinical toxicity in localized cervical carcinoma by radio-induced apoptosis study in peripheral blood lymphocytes (PBLs). Radiation Oncology, 2009, 4:48, p. 1-7.*
JBP Barber, CML West, AE Kiltie, A Roberts, D Scott. Detection of Individual Differences in Radiation-Induced Apoptosis of Peripheral Blood Lymphoctyes in Normal Individuals, Ataxia Telangiectasia Homozygotes and Heterozygotes, and Breast Cancer Patients after Radiotherapy. Radiation Research, 2000, vol. 153, p. 570-578.*
S Baumann, SC Fas, M Giaisi, WW Muller, A Merling, K Gulow, L Edler, PH Krammer, ML Weber. Wogonin preferentially kills malignant lymphocytes and suppresses T-cell tumor growth by inducing PLCyl- and Ca2+-dependent apoptosis. Blood, 2008, vol. 111, No. 4, p. 2354-2363.*
NEA Crompton, M Ozsahin. A Versatile and Rapid Assay of Radiosensitivity of Peripheral Blood Leukocytes BAsed on DNA and Surface-Marker Assessment of Cytotoxicity. Radiation Research, 1997, vol. 147, p. 55-60.*
BD Biosciences. Introduction to Flow Cytometry: A Learning Guide, 2002, p. 1-52.*
M Cornelissen, J Phillippe, S De Sitter, L De Ridder. Annexin V Expression in apoptotic peripheral blood lymphocytes: An electron microscopic evaluation. Apoptosis 2002, vol. 7, p. 41-47.*
JBP Barber, CML West, AE Kiltie, SA Roberts, D Scott. Detection of Individual Differences in Radiation-Induced Apoptosis of Peripheral Blood Lymphocytes in Normal Individuals, ATaxia Telangiectasia Homozygotes and Heterozygotes, and Breast Cancer Patients after Radiotherapy. Radiation Research. 2000, vol. 153, p. 570-578.*
I Nicoletti, G Migliorati, MC Pagliacci, F Grignani, C Riccardi. A rapid and simple method for measuring thymocyte apoptosis by propidium iodid staining and flow cytometry. Journal of Immunological Methods. Jun. 1991, vol. 139, Iss 2, p. 271-279.*
S Baumann, SC FAs, M Giasi, WW Muller, A Merling, K Culow, L Edler, PH Krammer, M Li-Weber. Wogonin preferentially kills malignant lymphocytes and supresses T-cell tumor growth by inducing PLCy1- and Ca2+-dependent apoptosis. Blood, Feb. 15, 2008, vol. 111, No. 4, p. 2354-2363.*
CD Bortner, JA Cidlowski. Flow Cytometric Analysis of Cell Shrinkage and Monovalent Ions during Apoptosis. methods in Cell Biology, 2001, vol. 66, p. 49-67.*

(Continued)

*Primary Examiner* — John S. Brusca
*Assistant Examiner* — Olivia M Wise
(74) *Attorney, Agent, or Firm* — Hamre, Schumann, Mueller & Larson, P.C.

(57)    ABSTRACT

A screening method evaluates influence of a cytotoxic factor on lymphoid cells. The method includes administering or irradiating lymphoid cells with the cytotoxic factor that injures the lymphoid cells; incubating the lymphoid cells to which the cytotoxic factor is administered or irradiated for a selected time; measuring a cell size of the lymphoid cells after the incubation; and determining influence of the cytotoxic factor on the lymphoid cells based on a change of the cell size. According to this method, influence of radiation or a drug, or efficacy of radiation, a radiation-protecting agent, an antioxidant, a radiation-sensitizing agent, a drug, or ultraviolet rays can be evaluated economically and objectively in a short period of time.

7 Claims, 9 Drawing Sheets

(56) References Cited

OTHER PUBLICATIONS

Oyama (Ohyama) et al.: "Studies on heavy particle ray induced apoptosis"; Heisei 7 Nendo National Institute of Radiological Sciences Juryushisen Gan Chiryo Sochi to Kyodo Riyo Kenkyu Hokokusyo, No. 120 (1997), pp. 128-129—Induction of apoptosis in mouse L5178Y and L5178Y0S leukemia cells by HIMAC carbon ion beams.
Anazi et al.: "Heat-Treated Mineral-Yeast as a Potent Post-irradiation Radioprotector"; J. Radiat. Res., No. 49 (2008), pp. 425-430, http://jrr.jstage.jst.go.jp.
Tayama et al.: "Comet Assay Attempted with Silver Staining Method and Manual Microscopic Analysis Using Cho-Ki Cells"; Annual Report of Tokyo Metropolitan Institute of Public Health, 55 (2004), with partial translation (9 pages).
Kanda et al.: "Sister chromatid exchanges in ring chromosomes following X-irradiation of human lymphocytes"; International Journal of Radiation Biology., May 2004, vol. 80, No. 5, pp. 363-368.
Sekine et al.: "High LET heavy ion radiation induces lower numbers of initial chromosome breaks with minimal repair than low LET radiation in normal human cells"; Mutation Research-Genetic Toxicology and Environmental Mutagenesis 652 (2008), pp. 95-101.
Takahashi et al.: "Tori Lymph-kyu B Saibo DT40 o Mochiita Hoshasen Yuhatsusei Apoptosis no Kaiseki"; Proceedings of the Annual Meeting of the Japan Radiation Research Society (2002), vol. 45, p. 141 (3-C-24).

\* cited by examiner (A)

(B)

(A)

(B)

SCREENING METHOD, SCREENING KIT AND ANALYSIS PROGRAM

TECHNICAL FIELD

The present invention relates to a screening method, a screening kit, and an analysis program for screening drug efficacy or toxicity of, for example, a radiation-protecting agent, an antioxidant, a radiation-sensitizing agent, or a drug, or influence of radiation or ultraviolet rays.

BACKGROUND ART

The accident happened at Fukushima Daiichi Nuclear Power Station on Mar. 11, 2011 accompanying with Great East Japan Earthquake has brought increased public interests in radiation. Also, in Japan, cancer radiotherapies tend to increase in recent years, and more specific studies regarding a radiation-protecting agent that protects normal tissues from radiation, and a radiation-sensitizing agent intended for synergistically improving the therapeutic effect of cancer are demanded.

Many studies intended to protect tissues from injury by radiation have been made heretofore. At present, drugs that prevent radionuclides from being absorbed and depositing in a living body and urge discharge of the same, such as an iodine agent and a chelating agent are known. However, these are used exclusively for reducing massive internal exposure by a specific radioactive element, and efficacy for low internal exposure or external exposure that can occur in a medical treatment is not observed. As famous examples of a drug intended to protect normal tissues in radiotherapy of tumors, cysteamine and amifostine are known. However, these drugs have difficulty in common use because of the side effect or the like. Also, many precedent studies on a radiation-sensitizing agent have been performed, but there is no radiation-sensitizing agent that is actually applied in clinical sites.

Under such circumstances, it is urgently demanded to develop effective radiation protecting and mitigating agents, and radiation-sensitizing agents. For rapidly developing such drugs, it is necessary to rapidly screen candidate drugs.

Here, various methods have been proposed for screening influence of an object to be investigated on human beings or animals such as influence by irradiation with radiation, effect of a drug, toxicity of a drug and so on. Screening methods that have been already proposed will be described below.

<Conventional Method 1: Screening Method Based on Survival Rate of Experimental Animal Such as Mouse or Rabbit>

This method is a method for screening influence of an object to be investigated on an experimental animal including subjecting an experimental animal such as mouse or rabbit to irradiation with radiation, drug administration or the like, and then measuring the survival rate of the experimental animal (see Non-Patent Document 1).

This method has the following problems. That is, it requires 20 days to 30 days of experimental period. Since the number of samples examinable at a time is limited to about one sample, and several tens of animals are required for examination of one sample, the method requires much cost. A large quantity of drug, which is equal to or more than about 10 times the concentration in an in vitro experiment, is required in administering an experimental animal with the drug. Therefore, it is difficult to prepare samples, particularly, in early stages of new drug development. It is largely affected by individual differences of experimental animals.

<Conventional Method 2: Comet Assay Method>

This method is an assay of detecting a DNA fragment occurring by irradiation with radiation, drug administration or the like as a length of a tail that looks like a comet (see Non-Patent Document 2). The basic principle is as follows. That is, DNA is caused to migrate in an agarose gel by electrophoresis, and observed under a microscope. The cell having experienced a cut among the migration cells looks like a comet. This migration cell consists of a head part composed of a nuclear region, and a tail part composed of a DNA strand that is loosened by the cut and migrates to the anode. Variation in DNA migration amount depends on various factors including the agarose concentration of the gel, pH, temperature, and voltage, current and running time in the electrophoresis. This method is also employed as a method for identifying a toxic substance in toxicity evaluation assays of foods and chemicals, and researches on health effects.

This method has the following problems. That is, it requires 2 days to 3 days of experimental period. Since the method includes a large number of manipulation steps and requires time for the manipulation, the number of samples that can be examined at a time is about ten at most. It is costly because dedicated gels and reagents are required.

<Conventional Method 3: PCC Method>

This PCC (Premature chromosome condensation) method is a method of counting the number of chromosomes by observation under a microscope to identify injury of chromosomes qualitatively and quantitatively, in estimation of an exposure dose of an individual (see Non-Patent Documents 3, 4).

This method has the following problems. That is, it requires about one week of experimental period. Since the process requires time, the number of samples that can be examined at a time is about ten at most. It includes many manipulation steps. Visual check under a microscope by man power leads fatigue in data analysis. Visual check under a microscope by man power tends to involve a subjective view.

<Conventional Method 4: Multicolor FISH Method>

By combining the aforementioned PCC method (Conventional method 3) and a Multicolor FISH (Fluorescence in situ hybridization) method, it is possible to observe the details of injury of chromosome. Here, the Multicolor FISH method is a method for discriminating all chromosomes in a single hybridization manipulation. Probes that will specifically bind with respective chromosomes are provided, and each probe is labeled with a combination of five colors of fluorescent dyes so that the combination of fluorescent wavelengths differs between chromosomes. Each chromosome is discriminated according to the combination.

This method has the following problems. That is, it requires about one week of experimental period, and takes a time until the result is obtained. The number of samples that can be examined at a time is about one at most. Visual check under a microscope by man power leads fatigue in data analysis. Visual check under a microscope by man power tends to involve a subjective view. It is costly because it requires expensive probes or the like.

<Conventional Method 5: MTT Assay Method>

MTT (3-[4,5-dimethylthiazol-2-yl]-2,5-diphenyltetrazolium bromide) is used in checking influence and toxicity on cell growth. MTT, which is water-soluble and forms a yellow solution, turns into formazan by a dehydrogenase existing in mitochondria in cells after it is incorporated into the cells, and deposits as non-aqueous blue crystals. This deposit turns into a reddish violet solution when it is solved in an organic solvent such as DMSO (dimethyl sulfoxide), and thus the growth rate and survival rate of the cells can be determined as a mitochondria enzyme activity by absorbance at 450 nm. For example, in the case of HeLa cells (cells derived from human cervical cancer) having a doubling time of 24 hours, a MTT treatment is performed at a fixed time everyday (every 24 hours), and a growth curve of the cells can be determined from the measurements by a plate reader.

This method has the following problems. That is, it requires 3 days to 14 days of experimental period, and takes a time until the result is obtained. Also, much cost is required for reagents.

<Conventional Method 6: Trypan Blue Staining Method>

In this method, cells are stained with Trypan Blue (Trypan Blue tetrasodium; 3,3'-[(3,3'-dimethyl-4,4'-biphenylene)bis(azo)]bis[5-amino-4-hydroxy-2,7-naphthalene diphosphonate] dye, and apoptotic cells are counted with a hemocytometer (Neubauer hemocytometer) to detect cytotoxicity. Trypan Blue passes through a cell membrane having injury and stains an apoptotic cell blue, but it does not stain a normal cell having a perfect membrane. By counting the cells stained blue, it is possible to quantify the apoptosis.

This method has the following problems. That is, it requires 3 days to 7 days of experimental period, and takes a time until the result is obtained. The number of samples that can be examined at a time is about three at most. Visual check under a microscope by man power leads fatigue in data analysis. Visual check under a microscope by man power tends to involve a subjective view.

<Other Proposed Conventional Method>

Also, a method of screening a molecule that reduces apoptosis of cells is proposed (see Patent Document 1). In this method, Mcl-1 null MEF cells are seeded onto a flat-bottomed 96-well plate, and after 12 hours to 24 hours, a library compound is added at final concentrations of 0.1 µM, 1 µM, and 10 µM, and incubated for 2 hours, followed by addition of ABT-737 (100 nM) or a carrier medium, and cell viability is scored 24 hours later by using AlamarBlue dye and read 4 hours later.

This method has the following problems. That is, it requires at least about 2 days of experimental period, and takes a time until the result is obtained. Since the AlamarBlue dye or the like is used, time and labor are required for the manipulation.

As described above, any conventional method has at least one of the problems of taking a time for obtaining a result, requiring much cost, and susceptibility to a subjective view. There has been no method that can solve all of these three problems.

PRIOR ART DOCUMENTS

Patent Document

Patent Document 1: Japanese Patent Application Laid-open No. 2010-521183

Non-Patent Documents

Non-Patent Document 1: K. ANZAI, et. al., Journal of Radiation Research. 49: 425-430, 2008
Non-Patent Document 2: S. TAYAMA et. al., Annual report of Tokyo Metropolitan Institute of Public Health. 55: 315-318, 2004
Non-Patent Document 3: R. KANDA. et. al., International Journal of Radiation Biology 80: 363-368, 2004
Non-Patent Document 4: E. Sekine, et. al., Mutation Research—Genetic Toxicology and Environmental Mutagenesis. 652: 95-101, 2008

SUMMARY OF THE INVENTION

Problems to be Solved by the Invention

In light of the aforementioned problems, it is an object of the present invention to provide a screening method, a screening kit, and an analysis program capable of performing economical and objective measurement in a short period of time.

Solutions to the Problems

The present invention provides a screening method including: administering or irradiating lymphoid cells with a cytotoxic factor that injures the lymphoid cells; incubating the lymphoid cells administered or irradiated with the cytotoxic factor for a predetermined time; measuring cell size of the lymphoid cells after the incubation; and determining influence of the cytotoxic factor on the lymphoid cells based on the cell size. The preset invention can also provide a screening kit, and an analysis program used for the screening method.

Effects of the Invention

According to the present invention, it is possible to provide a screening method capable of performing economical and objective measurement in a short period of time.

EMBODIMENTS OF THE INVENTION

Figure 1:
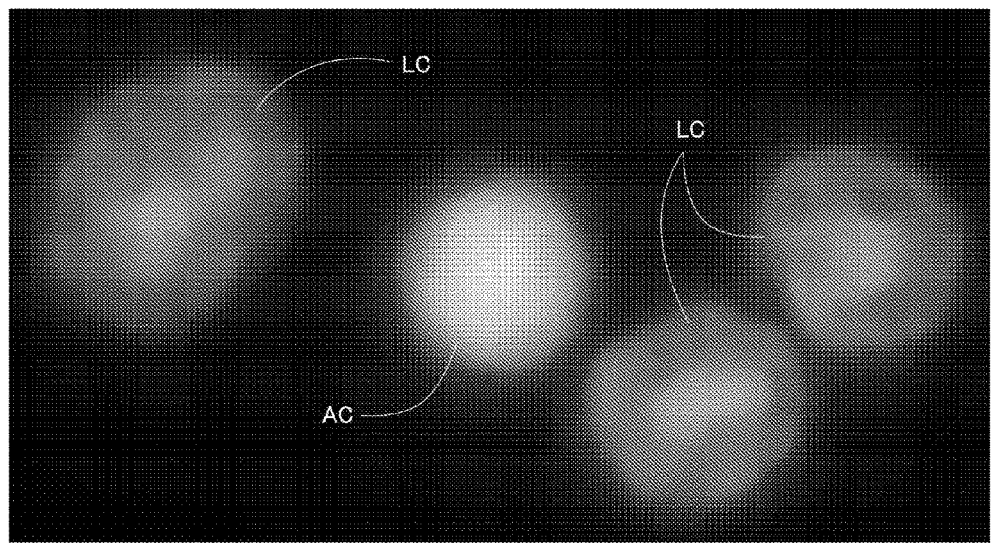
FIGS. 1(A) and 1(B) are explanatory diagrams of normal thymocytes and a thymocyte condensed as a result of apoptosis.
Figure 1:
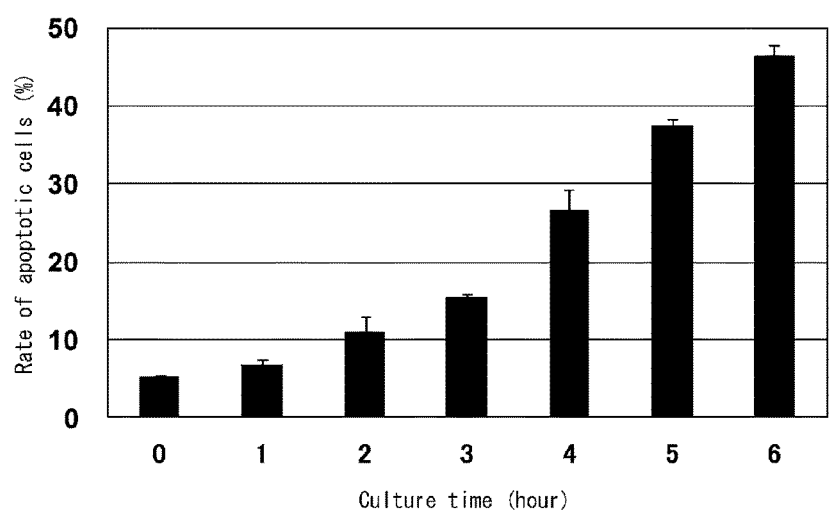

Hereinafter, one embodiment of the present invention will be described with reference to the attached drawings.

In the research laboratory to which the present inventors belong, a large number of new agents are designed and synthesized in respect of candidate drugs or compounds for a radiation-protecting agent or a radiation-sensitizing agent. However, the existent methods capable of determining efficacy or toxicity of a new drug thus designed and synthesized require much cost and time, and hence they are not appropriate for screening a large number of new drugs.

For this reason, the present inventors have made diligent studies for screening a clinically applicable drug having high efficacy. The inventors have invented a screening method capable of making objective determination for many drugs in a short period of time. This screening method is named "NILTH-ACCA (Nirs Lymph Thymus-Apoptosis Clear Check Assay)".

With this screening method (NILTH-ACCA, the same shall apply hereinafter), even for a candidate compound for a radiation-protecting agent whose antioxidative ability or radical eliminating ability is verified only chemically, it is possible to evaluate its function biologically. In other words, this screening method enables verification of the radiation-protecting effect using an organism (living body), and provides a pipeline that connects chemistry such as drug manufacturing and synthesis, and biology for examining actual influence on a living body. Therefore, it can be an established method for determining the effect of a radiation-protecting agent or a radiation-sensitizing agent. Also, this screening method can measure or estimate not only radiation, but also influence and toxicity of a cytotoxic factor (radiation, ultraviolet rays, or a drug (candidate drug) etc.), effect of a drug on the cytotoxic factor, and degree of sensitivity or injury of an individual (or individual person) to the cytotoxic factor.

The screening method of the present invention is carried out mainly by the following four steps.

[Step 1] Preparation of lymphoid cells
[Step 2] Irradiation or administration of object to be screened
[Step 3] Incubation for a predetermined time
[Step 4] Measurement of cell size Each step will be described in detail.

Hereinafter, when the terms "lymphoid cell", "thymocyte", "leucocyte", and "lymphocyte" are used, they mean plural cells rather than one cell in manipulation processes. In other words, a plurality of cells (lymphoid cells, thymocytes, leucocytes, lymphocytes) are irradiated or administered with an object to be screened, and incubated, and subjected to cell size measurement.

[Step 1] Preparation of Lymphoid Cells

Lymphoid cells are cells of lymphatic system including thymocytes that can be isolated from thymus, leucocytes and lymphocytes that can be isolated from peripheral blood, and myelocytes that can be isolated from bone marrow. Lymphocytes may be used as they are, or those classified into NK cells, T cells, NKT cells, B cells and the like by a technique of fluorescence staining or the like may be used. When those classified are used, more specific examination can be made. In future, lymphoid cells such as thymocytes, lymphocytes, or myelocytes may be differentiated by induction from ES (Embryonic stem) cells or iPS (induced pluripotent stem) cells. Also, tissues containing lymphoid cells may be used without isolation of lymphoid cells, for example, as is the use of blood containing lymphocytes.

Lymphoid cells may be used as they are, however, they are preferably subjected to an appropriate treatment for improving the measurement accuracy.

In the case of thymocytes, for example, the thymus is surgically removed from an animal such as a rat, mouse, rabbit or monkey, and washed with a washing solution, and then the thymus is put into a commonly-used culture medium supplemented with serum to squeeze thymocytes. The thymocytes are passed through mesh to remove unnecessary contaminants and to disassemble the cells.

In the case of lymphocytes, sampled peripheral blood is mixed with an anticoagulant and a reagent for separating lymphocytes, and then the resultant solution is centrifuged to separate lymphocytes, and the resultant cells are put into a commonly-used culture medium supplemented with serum.

In the case of myelocytes, myelocytes are extracted from the lumen of excised femur, and suspended in a commonly-used culture medium supplemented with serum.

In the case of leucocytes, an anticoagulant and a hemolytic agent are added to sampled blood, and the resultant solution is left still at room temperature for a certain time under light-shielded condition, and then centrifuged, and the supernatant is removed by aspiration, and the resultant pellet is dissolved in a culture medium supplemented with serum, and the resultant solution is passed through mesh to remove unnecessary contaminants and to disassemble the cells, and then put into a commonly-used culture medium supplemented with serum.

In the case of blood, an anticoagulant is added to sampled blood, and the resultant blood is put into a commonly-used culture medium supplemented with serum.

The washing solution for use in washing is a solution having pH, osmotic pressure and the like adjusted so as not to inflict damage on cells, e.g., buffered saline or phosphate buffer. As the solution used herein, those having an osmotic pressure which is the same as that of a cell are used so that they are not hypotonic or hypertonic to the cell. As the buffered saline, those not containing a surfactant, or those containing a surfactant in such a small concentration that will not pierce the cell membrane can be used, and specifically, PBS (Phosphate Buffered Saline), TBS (Tris-Buffered Saline) or the like can be used.

As the serum, appropriate serum capable of culturing cells can be used. For example, fetal bovine serum (FBS) or horse serum can be used, and the concentration of which ranges from 1 to 100%. It is recommended to subject these serums to an inactivating treatment, such as a treatment in a water bath at 56° C. for 30 minutes, for deactivating complement components in the serum. Serum substitutes and the like (such as an auxiliary reagent for a serum-free medium containing a growth factor) can also be used.

As the culture medium, a liquid medium for culture cell of mammals can be used, and not only natural components, but also a synthetic culture medium that can be prepared exclusively from purified chemicals may be used. Concrete examples of the culture medium that can be used include RPMI 1640 (Roswell Park Memorial Institute 1640) medium, D-MEM (Dulbecco's Modified Eagle Medium), MEM (Minimum Essential Medium), αMEM (alpha Modified Eagle Minimum Essential Medium), F12 (Nutrient Mixture F-12 Medium), and McCoy 5A (McCoy's 5A Medium). As the culture medium, it is preferred to use a medium in which the degree of condensation of lymphoid cells by a cytotoxic factor increases, and a medium in which the area is condensed to at least approximately 70% of that of normal lymphoid cells can be used, and a medium in which the area is condensed to at least approximately 60% is preferred, and a medium in which the area is condensed to at least approximately 50% or less is more preferred. This area corresponds to the area of a cell viewed from a certain direction and is measured as the size of shade of a cell with respect to light by flow cytometry.

The lymphoid cells thus obtained are counted and a necessary number of the cells are seeded on a plate. The necessary number herein is preferably the number that is enough to compare the distribution of cell numbers of cell size where the number of cells peaks and/or each cell size, for untreated lymphoid cells and for treated lymphoid cells. A control sample of untreated lymphoid cells means cells incubated for a predetermined time in a culture medium supplemented with serum, but without addition of a drug or radiation. In other words, the control is treated in the completely same conditions except for addition of a drug or radiation.

[Step 2] Irradiation or Administration with Object to be Screened

The plural lymphoid cells seeded on a plate are irradiated or administered with an object to be screened. For example, when the object to be screened is a radiation-protecting agent or a radiation-sensitizing agent, the lymphoid cells are administered with the radiation-protecting agent or the radiation-sensitizing agent and irradiated with radiation (protection target of object to be screened). In the case of screening toxicity of a drug (object to be screened), the lymphoid cells are administered with the drug. When an antioxidant (a kind of radiation-protecting agents) is the object to be screened, administration of the antioxidant to the lymphoid cells, and irradiation with radiation or addition of a hydrogen peroxide solution that adds oxidation stress to the cells are performed.

During Step 1 and Step 2, the temperature of the culture medium containing the lymphoid cells can be set within the range of 3° C. to 26° C., preferably approximately 4° C. to 25° C., and more preferably approximately 4° C.

The treatment after introduction of lymphoid cells (or tissues containing lymphoid cells) into the culture medium in Step 1 until completion of Step 2 can be carried out in about 1 hour to 2 hours, and thus the time during which the lymphoid cells are in the culture medium is also about 1 hour to 2 hours.

[Step 3] Incubation of Predetermined Time

Incubation is performed for a time enough for lymphoid cells to undergo apoptosis and condense by stimulation of a cytotoxic factor. This incubation time (indicating a cell culture time after irradiation or administration with an object to be screened, the same shall apply hereinafter) is preferably 2 hours or more, more preferably 2 hours to 6 hours, further preferably 3 hours to 5 hours, and most preferably about 4 hours. In Step 3, the lymphoid cells are in the culture medium for a time equivalent to this incubation time. This incubation time is counted from the point of time when the culture medium containing lymphoid cells is placed in an environment at incubation temperature.

The temperature of the culture medium during incubation can be 3° C. to 41° C., preferably 4° C. to 40° C., and more preferably approximately 37° C. The pH is preferably pH 6 to pH 8, and more preferably approximately pH 6.8±0.5.

During this incubation, lymphoid cells undergo apoptosis under the influence of a cytotoxic factor (a protection target of the object to be screened, or the object to be screened itself) and the cell size decreases due to condensation at that time.

Hereinafter, condensation of lymphoid cells under the influence of a cytotoxic factor will be described by practicing Step 1 to Step 4. FIG. 1(A) shows a DAPI (4',6-diamidino-2-phenylindole) fluorescence stained image for explaining condensation of cell size. This figure is imaged under a fluorescent microscope through an objective lens at a 100-fold magnification after staining the nuclei of the thymocytes.

As shown in the figure, a chromatin structure which is a complex of DNA and protein existing in a eukaryotic cell is observed in a nucleus of a living cell (LC). In an apoptotic cell (AC) having experienced apoptosis by a cytotoxic factor, the concentration of a nucleus is observed. In this way, by utilizing the property of a cell that it condenses without forming an apoptotic body generated by fragmentation of the cell, it becomes possible to measure the presence or absence of apoptosis by measuring the cell size.

FIG. 1(B) is a graph illustrating behavior regarding the rate of apoptotic cells in the thymocytes depending on the culture time (incubation time). This graph shows the rate of apoptotic cells measured by flow cytometry after a lapse of a culture time of a certain period after irradiating rat thymocytes prepared through Steps 1 to 2 with 2 Gy X-ray. Concretely, measurement is made while only incubation time is varied from 0 to 6 hours in unit of one hour by using the protocol of Example 1 described later. In this graph, the horizontal axis represents the incubation time, and the vertical axis represents the rate of the number of apoptotic cells to the entire number of cells. As illustrated, it can be seen that the rate of apoptosis increases depending on the incubation time.

[Step 4] Measurement of Cell Size

After incubation, the cell size of the lymphoid cells is measured. The present screening method detects apoptosis of the lymphoid cells by change in the cell size of the lymphoid cells, namely a reduction in cell size due to condensation. This measurement of the cell size for detecting apoptosis can be performed by comparing the distribution of cell size before change and the distribution of cell size after change for plural lymphoid cells.

The cell size before change that is a basis for comparison is (1) the cell size of untreated (only irradiation or administration with an object to be screened in Step 2 is not performed, and any of other Steps 1, 3 and 4 are performed) lymphoid cells (control cell size), (2) the cell size of intact lymphoid cells not subjected to Step 3, or (3) cell size preliminarily measured by (1) or (2) and specified as a reference. Among these, (1) the cell size of untreated lymphoid cells, with which only the change caused by irradiation or administration with an object to be screened can be checked, is preferred.

The comparison of the distributions of the cell size can be made by appropriate methods, concretely by measurement based on the presence or absence and degree of shifting of the peak part of cell size in distribution, or measurement based on the presence or absence and degree of change in the distribution area of cell size, or measurement based on the presence or absence and degree of change in the cell number of original cell size.

The cell size to be measured can be the size of a whole cell of a lymphoid cell or the size of the nucleus of a lymphoid cell, or both of these. Since the size of a whole cell is preferred because the degree of condensation is enlarged, the size of a whole cell is measured in Example 1 to Example 4 described later.

The measurement and comparison of the cell size can be made by the area of a cell, the volume of a cell or the length of a cell in accordance with a device for measurement. The length of a cell can be an appropriate length such as the maximum length in a certain direction viewed from a certain view point (for example, maximum length in the width direction in which a cell-containing fluid flows), the major axis of a cell, the minor axis of a cell, the diameter of a cell, or the radius of a cell. The area can make discrimination more clearly than the length, and the volume can make discrimination more clearly than the area. The area or length can be measured more easily as compared with the volume. Therefore, the area can achieve both clearness of difference and easiness of measurement.

This measurement may be performed by a device capable of measuring the size of a cell, such as a flow cytometry, a cell counter or a blood cell measurement device (hemocytometer). In Example 1 to Example 4 described later, FACSCALIBUR™ (a flow cytometry system) (BD, Becton, Dickinson and Company) which is one type of flow cytometry is used for measurement, and the area of a cell is measured as the cell size. This area is an area when a cell is viewed from a certain direction, and can be measured by flow cytometry as the size of shade of the cell to light.

By measuring the cell size in this manner, it is possible to screen the presence or absence and degree of influence by irradiation or administration with the object to be screened.

Since this measurement by flow cytometry can be performed in 30 seconds to 2 minutes for one sample, the lymphoid cells are in the culture medium during this period. Preferably, the sample is cooled, for example, by putting the plate or tube containing the sample on ice during the measurement after end of incubation.

Hereinafter, concrete examples by Step 1 to Step 4 will be described. Example 1

As Example 1, an example using thymocytes as lymphoid cells will be described. In this example, rat thymocytes are used. A rat is suited for studies of screening and the like because a rat has the thymus larger than that of a mouse, and a large quantity of thymocytes corresponding to 2000 to 20000 samples is obtained from one rat.

[Step 1] Preparation of Lymphoid Cells (Thymocytes, in this Example)

(1) First, extract the thymus surgically from a rat.

(2) The extracted thymus is washed lightly in PBS. This washing may be performed for 1 minute to 5 minutes, and actually for 2 minutes to 3 minutes merely for washing out excess blood or tissues.

(3) The washed thymus is put into a RPMI 1640 medium supplemented with approximately 10% FBS (fetal bovine serum) (having subjected to an inactivation treatment). As the inactivation treatment, a heat treatment at 56° C. is performed for 30 minutes. In the example, the RPMI 1640 medium is 500 ml (ml is a unit symbol for milliliter, the same shall apply hereinafter), and FBS is 55 ml. Thereafter, the thymocytes are kept in the RPMI 1640 medium supplemented with serum to improve the separating ability of the presence or absence of condensation, and improve the measurement accuracy.

(4) Thymocytes are squeezed out of the thymus with tweezers, and passed through mesh to remove unnecessary contaminants and to disassemble the thymocytes. The culture temperature during this treatment is 4° C., and pH is 6.8. The amount of the medium used during cell purification is approximately 20 ml.

(5) The number of cells is counted, and a required number of the cells are seeded on a plate. In the experiment of this example, $5 \times 10^5$ cells/well are seeded using a 48-well plate. Also, since measurement is performed for about 20 samples in the experiment of this example, approximately 10 ml of a medium is used. As the medium, a medium of the volume conforming to the container is required. For example, when a 48-well plate is used, approximately 500 µl/well (microliter per well) is required in seeding cells on the plate. When a 96-well plate is used, approximately 50 to 200 µl/well is required in seeding cells on the plate. When one 96-well plate is used, up to approximately 20 ml of a medium is required.

[Step 2] Irradiation or Administration with Object to be Screened

In this example, (I) irradiation with 2 Gy X-ray, (II) administration with a 1 mM (mM is a unit symbol for millimolar, the same shall apply hereinafter) catechin derivative, (III) preliminary administration with a 1 mM catechin derivative and irradiation with 2 Gy X-ray, (IV) administration with 100 µM epigallocatechin (µM is a unit symbol for micromolar, the same shall apply hereinafter), (V) administration with 10 µM vitamin C, or (VI) administration with 100 µM vitamin C was performed. The temperature of the medium in performing this treatment can be 4° C. to room temperature, and is preferably approximately 4° C. so as not to promote the reaction. Gray (Gy) is a unit for absorbed dose of radiation. The absorbed dose when 1 joule of radiation energy is absorbed in 1 kilogram of a substance by radiation is defined as 1 gray.

[Step 3] Incubation for Predetermined Time

The samples of (I) to (VI) in Step 2 were incubated for 4 hours. During the incubation, the medium is at a temperature of 37° C., at a $CO_2$ concentration of 5%, under humidification, and at pH 6.8.

[Step 4] Measurement of Cell Size

Figure 2:
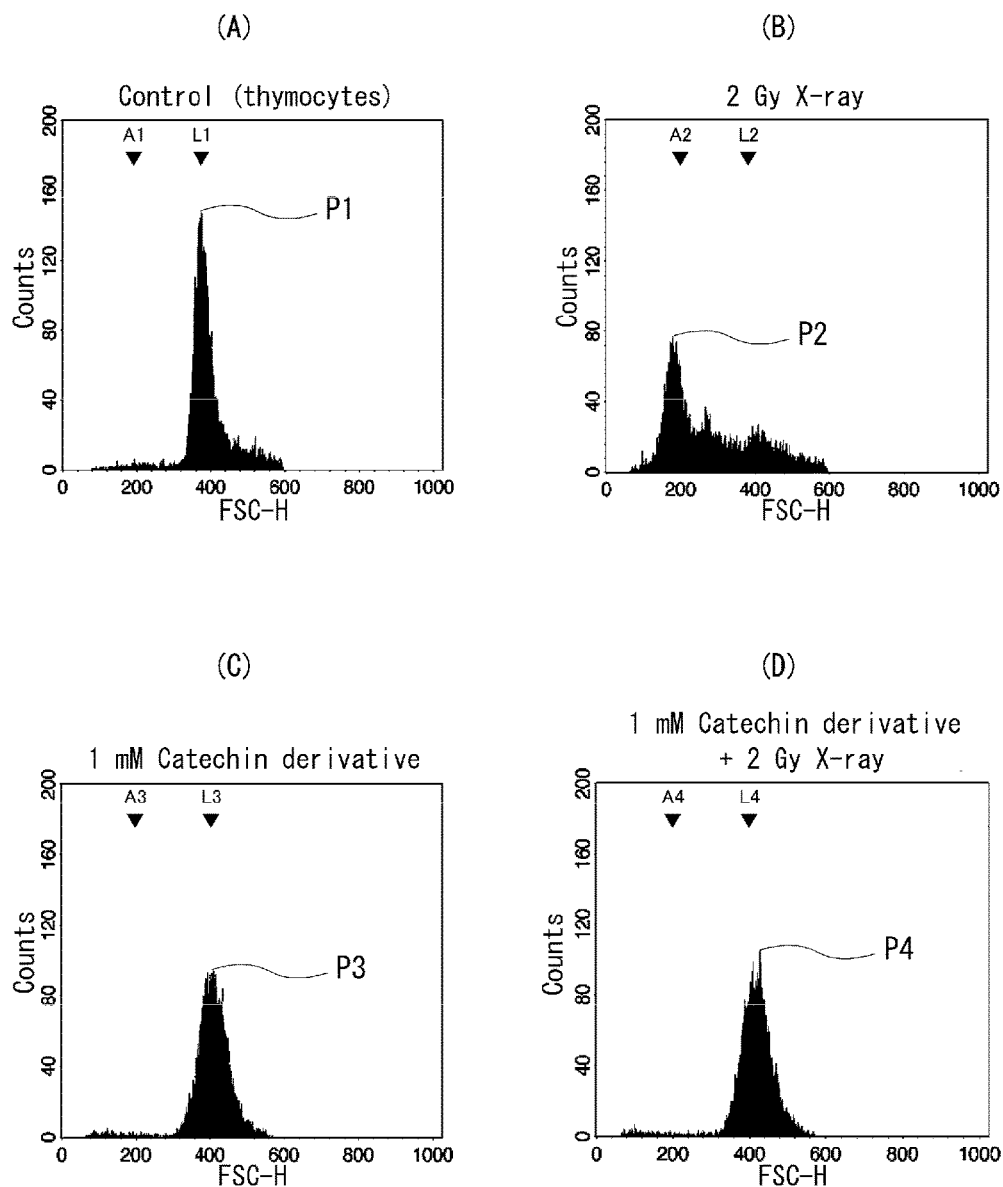
FIGS. 2(A) to 2(D) are explanatory diagrams for influence of radiation on thymocytes according to cell size measurement graphs.
Figure 3:
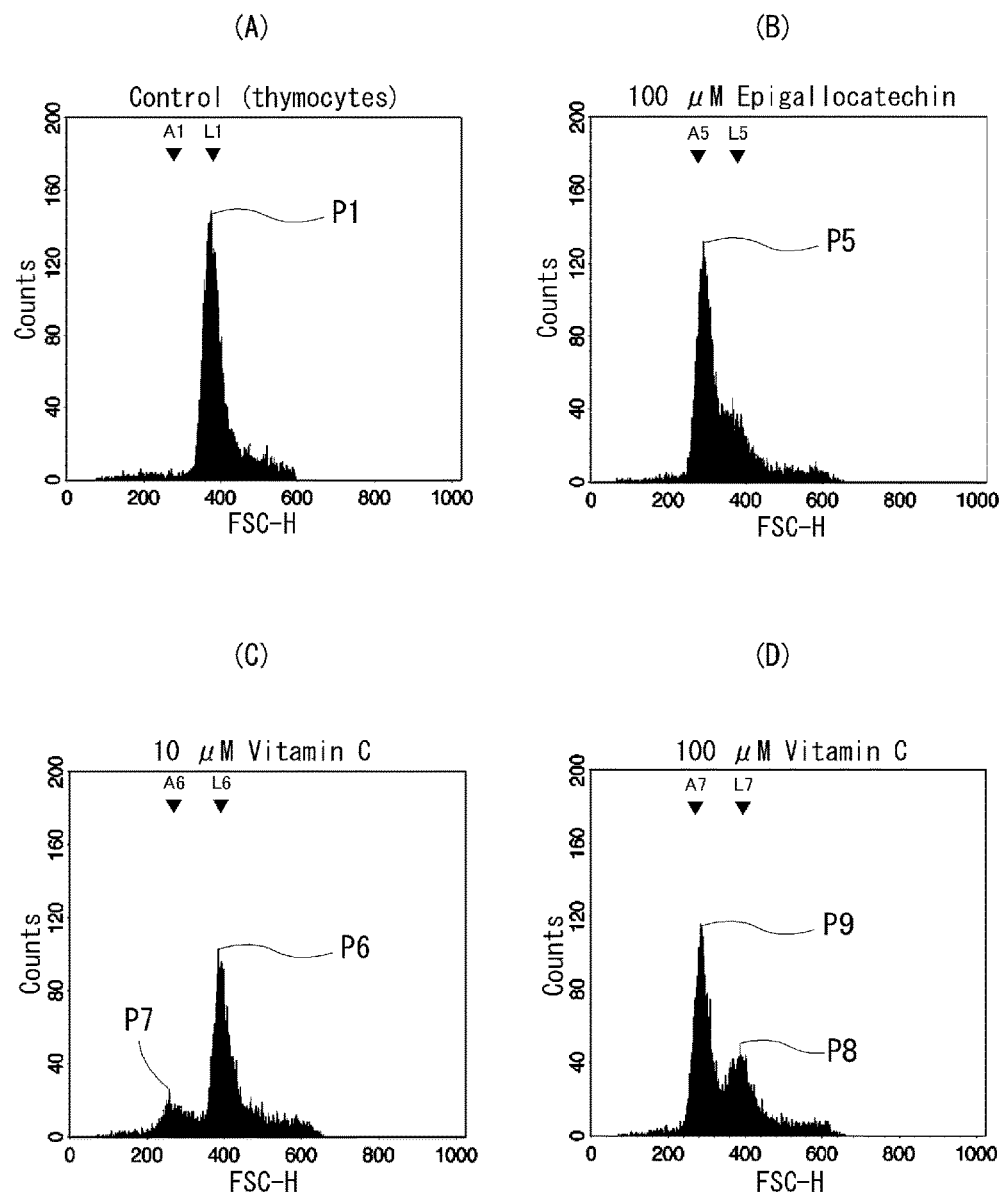
FIGS. 3(A) to 3(D) are explanatory diagrams for drug toxicity on thymocytes according to cell size measurement graphs.

After the incubation in Step 3, measurement was performed by using FACSCALIBUR™ (a flow cytometry system). The time required for the measurement is about one hour. During the measurement, the plate containing the sample was placed on ice to cool the sample. The measurement results are shown in FIG. 2 and FIG. 3.

FIG. 2(A) to FIG. 2(D), and FIG. 3(A) to FIG. 3(D) are cell size measurement graphs showing measured cell sizes. In the cell size measurement graph, the horizontal axis represents the cell size, and the vertical axis represents the number of cells.

FIG. 2(A) is a cell size measurement graph of untreated thymocytes. As illustrated, peak P1 of the cell size is found around 400. Here, in the flow cytometry of the present example, numerical values of the horizontal axis are set so that living cell peak position L1 where the cell size of control (untreated thymocytes) peaks is found around 400. In this setting, the peak of the cell size of thymocytes having experienced apoptosis in this example is found at apoptotic cell peak position A1. Also in other FIG. 2(B) to FIG. 2(D), FIG. 3(A) to FIG. 3(D), measurement is performed with the same setting so that living cell peak position L (L1 to L7) is found around 400. It is only required that apoptotic cell peak position A (A1 to A7) is found at the position indicating smaller size than living cell peak position L (L1 to L7), and may be found at appropriate positions, for example around 200, around 250, or around 300.

FIG. 2(B) is a cell size measurement graph of thymocytes subjected to irradiation with 2 Gy X-ray. In this case, peak P2 is found around 200. In other words, no peak is found around 400 of living cell peak position L2, and peak P2 appears around 200 of apoptotic cell peak position A2 where no peak is found in the control. Comparison between FIG. 2(B) and FIG. 2(A) reveals that when thymocytes are irradiated with 2 Gy radiation in Step 2 using the aforementioned protocols of Step 1 to Step 4, the thymocytes condense due to irradiation, and the cell size of the thymocytes halves. Therefore, according to the present screening method, it is possible to identify the cytotoxic factor such as radiation as a substance that induces apoptosis in lymphoid cells.

From this fact, if the position of peak P1 of thymocytes measured without performing Step 2 is found around 200 (or smaller than around 400 which is living cell peak position L2) which is apoptotic cell peak position A2 despite the same setting of flow cytometry, it can be estimated that the living body before removal of the thymus is influenced by exposure to radiation or toxicity, and apoptosis of the thymocytes is induced.

FIG. 2(C) is a cell size measurement graph of thymocytes administered with a 1 mM catechin derivative. Since toxicity by the catechin derivative is not observed, peak P3 remains around 400 which is living cell peak position L3. Therefore, according to the present screening method, it is possible to identify the candidate as an atoxic substance that will not induce apoptosis of lymphoid cells in the concentration of this example having a radiation protecting effect.

FIG. 2(D) is a cell size measurement graph of thymocytes subjected to preliminary administration with a 1 mM catechin derivative and irradiation with 2 Gy X-ray. Peak P4 is found around 400 which is living cell peak position L4. That is, although peak P2 should shift to around 200 which is apoptotic cell peak position A4 as shown in FIG. 2(B) as a result of irradiation with radiation of 2 Gy, peak P4 remains around 400 (living cell peak position L4) as a result of preliminary administration with the catechin derivative, and no peak appears around 200 which is apoptotic cell peak position A4, revealing that condensation due to apoptosis does not occur. This suggests the radiation protecting effect of the catechin derivative. Therefore, according to the present screening method, it is possible to identify the candidate drug as a substance having a protecting effect against a cytotoxic factor (factor that induces apoptosis of lymphoid cells).

FIG. 3(A) is a cell size measurement graph of untreated thymocytes which is the same as that of FIG. 2(A).

FIG. 3(B) is a cell size measurement graph of thymocytes administered with 100 μM epigallocatechin. Peak P5 is found around 300 (apoptotic cell peak position A5). Comparison between FIG. 3(B) and FIG. 3(A) reveals that the peak shifts due to the toxicity of epigallocatechin.

FIG. 3(C) is a cell size measurement graph of thymocytes administered with 10 μM vitamin C Although peak P6 remains around 400 (living cell peak position L6), the count number reduces relative to the control shown in FIG. 3(A). In addition, while a peak was found only at living cell peak position L1 around 400 in the control of FIG. 3(A), another small peak P7 appeared at apoptotic cell peak position A6 around 250 which is smaller than living cell peak position L1 around 400 in FIG. 3(C). This reveals that vitamin C has low toxicity in 10 μM.

FIG. 3(D) is a cell size measurement graph of thymocytes administered with 100 μM vitamin C. Although there is peak P8 at the position of around 400 (living cell peak position L7), the count number significantly reduces relative to the control shown in FIG. 3(A). While a peak was found only at the position around 400 in the control of FIG. 3(A), another large peak P9 appeared at apoptotic cell peak position A7 around 250 which is smaller than the position around 400 in FIG. 3(D). This reveals that toxicity remarkably appears with 100 μM vitamin C In other words, FIG. 3(D) and FIG. 3(C) reveal that toxicity of vitamin C is insignificant in 10 μM, but remarkably appears in 100 μM. Therefore, according to the present screening method, it is possible to identify the candidate drug as a substance having toxicity that induces apoptosis of lymphoid cells, and to identify the concentration at which the toxicity appears.

As seen from Example 1, it is possible to perform screening of a radiation-protecting agent, an antioxidant, and a radiation-sensitizing agent, screening of toxicity of a drug, and screening of effect by a drug (efficacy of drug).

In the present screening method, the techniques in all steps are easy, and an excellent result is obtained by incubation of about 4 hours, and even manipulation including the preparatory manipulation and the measurement manipulation can be completed in about 6 to 8 hours. Therefore, the present screening method is a very high throughput assay in comparison with conventional methods that require many days to obtain a result. Therefore, according to the present screening method, it is possible to largely reduce the term required for searching for new drugs.

The present screening method achieves screening by measuring cell size by utilizing the fact that the cell size of lymphoid cells reduces as a result of apoptosis. Therefore, according to the present screening method, it is possible to perform objective screening with high reproducibility without being affected by the subjective view as is in the method of microscopic observation by a researcher.

Also, according to the present screening method, it is possible to accurately measure only the change in cell size purely because cell fragmentation into apoptotic bodies does not occur even at the time of apoptosis and the number of cells does not change. Therefore, it is possible to obtain a clear and accurate result.

Since the present screening method uses lymphoid cells that can be abundantly obtained from an experimental animal rather than screening one sample for one experimental animal such as a rat as is the conventional case, only a small amount of sample volume is required. In addition, no special reagent is required. Therefore, the method can be applied economically.

Also, according to the present screening method, measurement can be made without the necessity of labeling with a fluorescent dye or the like as preliminary preparations, and only preparation of lymphoid cells such as thymocytes is required, so that the method can be applied economically and conveniently.

Since it is not necessary to use a specific cell strain, it is possible to acquire constant data independently of change in properties during passage or cell cycle, and to make comparison with data after a lapse of long term (for example, after several decades) according to the same criterion. Therefore, it can be used as a worldwide standard method.

Also, by using a culture medium such as a RPMI 1640 medium supplemented with serum, it is possible to improve the ability of separating condensed cells and normal cells, and to improve the measurement accuracy. To be more specific, in an experiment using a Krebs-Ringer-phosphate solution (pH 7.4) rather than a culture medium like a RPMI 1640 medium supplemented with serum, the cell size of thymocytes after condensation was about 70% of the cell size of normal thymocytes. In contrast, when a culture medium like a RPMI 1640 medium supplemented with serum was used, the cell size of thymocytes after condensation decreased to about 50% of the cell size of normal thymocytes, and the separating ability was improved.

As seen from the above, the present screening method is a non-conventional epochal method having all of convenience, objectivity and rapidity, and can largely reduce the term and costs required for the research, and can improve the satisfaction of the researcher.

Example 2

Next, as Example 2, an example using leucocytes as lymphoid cells will be described. In this example, leucocytes of a rat are used.

[Step 1] Preparation of Lymphoid Cells (Leucocytes, in this Example)

(1) First, sample blood from a rat.

(2) An anticoagulant (0.5 M EDTA (ethylenediaminetetraacetic acid)-2Na) in an amount of 1/100 of the amount of the sampled blood, and a 1× hemolytic agent in an amount of 10 times the amount of the blood are added. In this example, 5 ml of blood, 50 µl (µl is microliter, the same shall apply hereinafter) of 0.5 M EDTA-2Na, and 50 ml of 1× hemolytic agent are used. As the anticoagulant, not only 0.5 M EDTA-2Na, but also any anticoagulant may be used. As the hemolytic agent, Cat #555899 of Becton, Dickinson and Company (BD) is used, however, any appropriate one may be used without limited to this.

(3) Leave still at room temperature for 15 minutes under light-shielded condition.

(4) Centrifuge at a rotation speed of 1500 rpm for 5 minutes.

(5) Remove the supernatant by aspiration to obtain a pellet, and dissolve the pellet in a RPMI 1640 medium supplemented with serum. As this medium, a RPMI 1640 medium supplemented with approximately 10% FBS (fetal bovine serum) (having subjected to an inactivation treatment), pH 6.8, as is the same with that in Example 1 is used. Thereafter, the leucocytes are kept in the RPMI 1640 medium supplemented with serum to improve the separating ability of the presence or absence of condensation and improve the measurement accuracy.

(6) Remove unnecessary contaminants and disassemble cells through mesh.

(7) Count the number of leucocytes, and seed a required number of cells on a plate.

[Step 2] Irradiation or Administration with Object to be Screeened

In this example, (I) the sampled leucocytes were irradiated with 10 Gy X-ray. The temperature of the medium in performing this treatment can be 4° C. to room temperature, and is preferably approximately 4° C. so as not to promote the reaction.

Also for the purpose of detecting ex post that a living body (rat) was irradiated with radiation, (II) measurement in leucocytes sampled from a rat subjected to whole body irradiation with 10 Gy X-ray was also employed. In brief, in the case of (II), no treatment is performed in this Step 2.

[Step 3] Incubation for Predetermined Time

Samples from (I) to (II) in Step 2 were incubated for 4 hours. During the incubation, the medium is at a temperature of 37° C., at a $CO_2$ concentration of 5%, under humidification, and at pH 6.8.

[Step 4] Measurement of Cell Size

Figure 4:
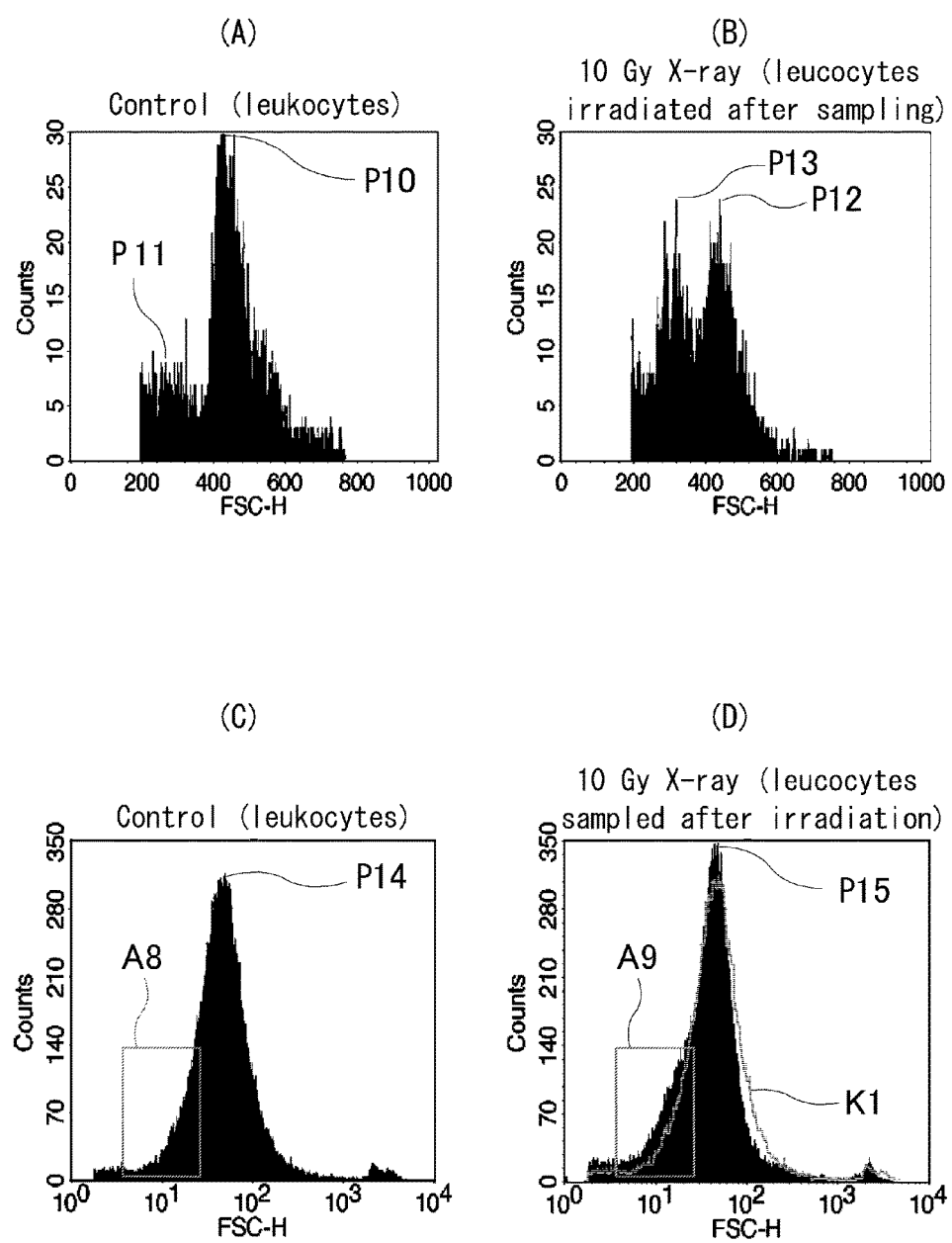
FIGS. 4(A) to 4(D) are explanatory diagrams for influence of radiation on leucocytes according to cell size measurement graphs.

After the incubation in Step 3, measurement was performed by using FACSCALIBUR™ (a flow cytometry system). The measurement result is shown in FIG. 4.

FIG. 4(A) to FIG. 4(D) are cell size measurement graphs showing measured cell sizes. In the cell size measurement graph, the horizontal axis represents the cell size, and the vertical axis represents the number of cells. In FIGS. 4(A) and 4(B), the horizontal axis is indicated by integer, and in FIGS. 4(C) and 4(D), the horizontal axis is indicated by index.

FIG. 4(A) is a cell size measurement graph of untreated leucocytes, and FIG. 4(B) is a cell size measurement graph of sampled leucocytes irradiated with 10 Gy X-ray in Step 2. As illustrated, peak P10 of the control shifts as a result of X-ray irradiation. To be more specific, as shown in FIG. 4(B), the count number of peak P12 of a little over 400 decreases in comparison with the control, and the count number of peak P13 around 300 increases in comparison with peak P11 of the control. The rate of apoptosis in this experimental result was 19.71% in the control, and 41.37% in irradiation with 10 Gy X-ray.

FIG. 4(C) is a cell size measurement graph of leucocytes sampled from an untreated rat, and FIG. 4(D) is a cell size measurement graph of leucocytes sampled from a rat subjected to whole body irradiation with 10 Gy X-ray. In this graph, on the graph after X-ray irradiation having peak P15 shown in black, the control shown in FIG. 4(C) is superposed as comparative line K1 shown in gray. As illustrated, the count number of cell population smaller than peak P14 of the control increases as a result of X-ray irradiation. To be more specific, the count number of cell population of apoptotic cell area A8 smaller than peak P14 of the control in FIG. 4(C) increases in the count number of cell population of apoptotic cell area A9 in the leucocytes of the rat subjected to X-ray irradiation in FIG. 4(D). In this experimental result, the rate of apoptosis was 54.71% in the control, and 65.00% in whole body irradiation with 10 Gy X-ray.

As seen from Example 2, the effect similar to that of the thymocytes in Example 1 can be obtained also in leucocytes.

In Example 2, the number of cells contained in the apoptotic cell fraction increases in FIG. 4. Therefore, it is also possible to further improve the measurement accuracy by performing further optimization, for example, by raising the ability to separate leucocytes, changing incubation conditions or measurement conditions, or analyzing only a specific cell group by combination with a fluorescent staining method although measurement was possible in the conditions of Example 2.

While a rat is used in Example 2, an equivalent effect can be obtained in leucocytes from blood sampled from other mammal or human being. Leucocytes from blood are available by sampling from a live animal individual.

Example 3

Next, as Example 3, an example using blood as lymphoid cells will be described. In this example, blood of a rat is used.

[Step 1] Preparation of Lymphoid Cells (Blood, in this Example)

(1) First, sample blood from a rat.

(2) An anticoagulant (0.5 M EDTA-2Na) in an amount of 1/100 of the amount of the sampled blood is added. In this example, 5 ml of blood, and 50 µl of 0.5 M EDTA-2Na are used. As the anticoagulant, any appropriate anticoagulant can be used without limited to 0.5 M EDTA-2Na.

[Step 2] Irradiation or Administration with Object to be Screeened

In this example, (I) the sampled blood was irradiated with 10 Gy X-ray. Also, for the purpose of detecting ex post that a living body (rat) was irradiated with radiation, (II) measurement in blood sampled from a rat subjected to whole body irradiation with 10 Gy X-ray was also employed. In brief, in the case of (II), no treatment is performed in this Step 2.

[Step 3] Incubation for Predetermined Time

Samples from (I) to (II) in Step 2 were incubated for 4 hours. During the incubation, the medium is at a temperature of 37° C., at a $CO_2$ concentration of 5%, under humidification, and at pH 6.8.

[Step 4] Measurement of Cell Size

Figure 5:
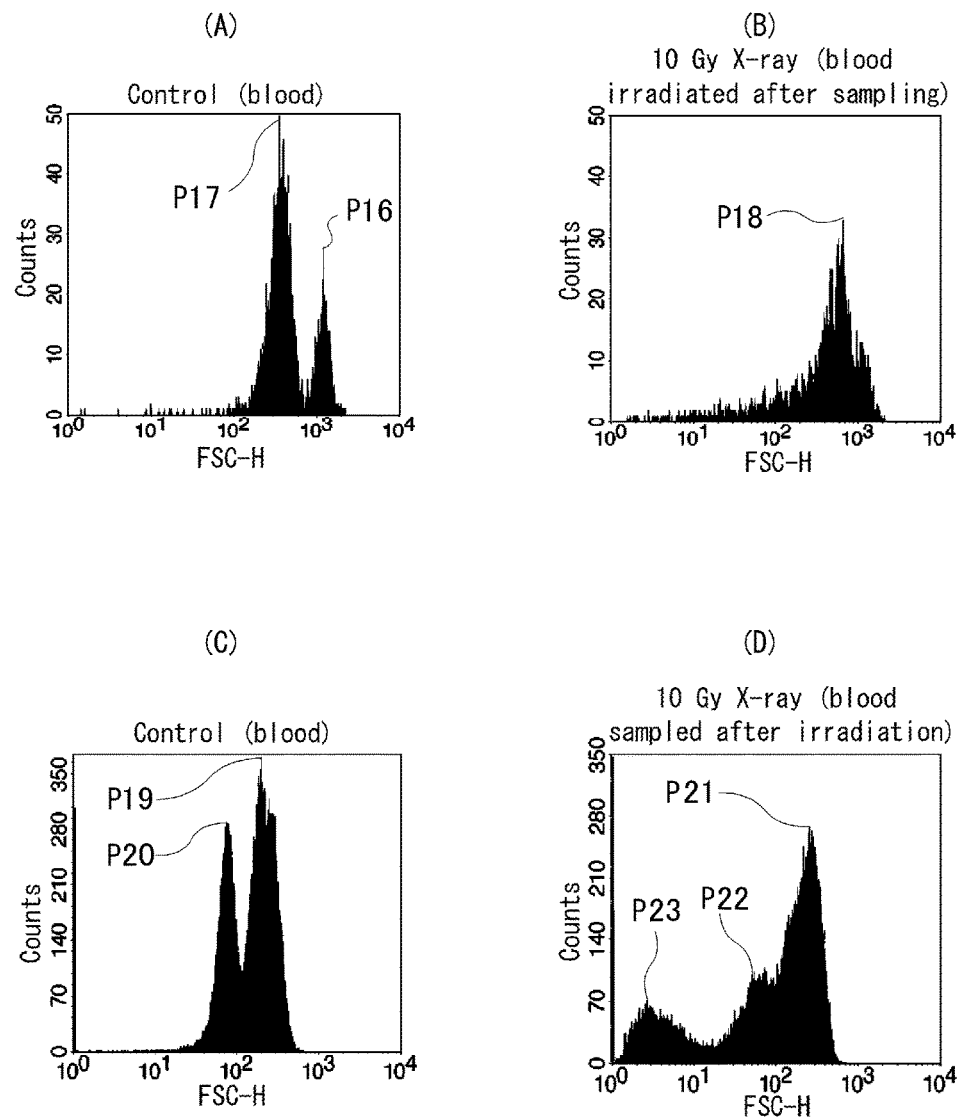
FIGS. 5(A) to 5(D) are explanatory diagrams for influence of radiation on blood according to cell size measurement graphs.

After the incubation in Step 3, measurement was performed by using FACSCALIBUR™ (a flow cytometry system). The measurement result is shown in FIG. 5. When the measurement sample has too high concentration to be adaptable to measurement by flow cytometry, the sample may be diluted into an appropriate concentration with a culture medium supplemented with approximately 10% FBS (fetal bovine serum) (having subjected to an inactivation treatment) as is the same with Example 1, a measurement solution for flow cytometry (e.g., sheath solution), PBS, or saline in this step.

FIG. 5(A) to FIG. 5(D) are cell size measurement graphs showing measured cell sizes. In the cell size measurement graph, the horizontal axis represents the cell size, and the vertical axis represents the number of cells. In FIG. 5(A) to FIG. 5(D), the horizontal axis is indicated by index.

FIG. 5(A) is a cell size measurement graph of untreated blood, and FIG. 5(B) is a cell size measurement graph of sampled blood irradiated with 10 Gy X-ray in Step 2.

As illustrated, the peak of the control shifts as a result of X-ray irradiation. To be more specific, as shown in FIG. 5(A), there is peak P16 around 1050 and there is second peak P17 around 400 in the control. In contrast, after X-ray irradiation, as shown in FIG. 5(B), only peak P18 around 700 is observed, and cell population having the sizes equal to or smaller than the same is observed in the shape of a ladder. This indicates that the peak around 400 is dispersed in the cell population having the sizes equal to or smaller than the same in the shape of a ladder as a result of apoptosis, and the peak around 1050 shifts to around 700 as a result of apoptosis.

FIG. 5(C) is a cell size measurement graph of blood sampled from an untreated rat, and FIG. 5(D) is a cell size measurement graph of blood sampled from a rat subjected to whole body irradiation with 10 Gy X-ray. As illustrated, peaks P19, 20 of the control shift as a result of X-ray irradiation. To be more specific, in the control of FIG. 5(C), first peak P19 around 250 and second peak P20 around 75 are observed, however, in the blood of the rat subjected to X-ray irradiation in FIG. 5(D), the peaks are dispersed into peak P21 around 250, peak P22 around 75, and peak P23 around 3. In this experimental result, the rate of apoptosis was 34.85% in the control, and 43.82% in whole body irradiation with 10 Gy X-ray.

As seen from Example 3, the effect similar to that of leucocytes in Example 2 can be obtained also in blood. In brief, while determination can be made by observing peaks of specific cells in the case of the specific cells such as thymocytes, leucocytes or lymphocytes, condensation of cells can be determined by examining not only such peaks but also the change in the whole cell size in the case of blood.

In Example 3, the number of cells contained in the apoptotic cell fraction increases in FIG. 5. Therefore, it is also possible to further improve the measurement accuracy by performing further optimization, for example, by changing incubation conditions or measurement conditions, or analyzing only a specific cell group by combination with a fluorescent staining method although measurement was possible in the conditions of Example 3. Dispersion of cell population observed in the measurement result of blood suggests the possibility of fragmentation of the cells. From this fact, by diluting in a culture medium such as a RPMI 1640 medium supplemented with serum before incubation, and keeping the blood thereafter in the culture medium such as a RPMI 1640 medium supplemented with serum, as optimization conditions, it is possible to prevent fragmentation of the cells and to improve the measurement accuracy.

While a rat is used in Example 3, an equivalent effect can be obtained in blood sampled from other mammal or human being. Blood is available by sampling from a live animal individual.

Example 4

Next, as Example 4, an example using lymphocytes as lymphoid cells will be described. In this example, lymphocytes of a rat are used.

[Step 1] Preparation of Lymphoid Cells (Lymphocytes, in this Example)

After performing the same treatment as in [Step 1] in Example 3, lymphocytes are isolated by using a lymphocyte isolation kit. As the lymphocyte isolation kit, for example, Lympholyte (registered trade name)-Mammal CL5115 available from COSMO BIO co., ltd. can be used, but any appropriate kit may be used without limited to this. During this isolation step, lymphocytes are put into a culture medium. As the culture medium, a RPMI 1640 medium supplemented with approximately 10% FBS (fetal bovine serum) (having subjected to an inactivation treatment), pH 6.8, as is the same with that in Example 1 is used.

The remaining [Step 2] to [Step 4] can be executed by performing the same treatments as in Example 2 or Example 3, and hence, detailed description thereof will be omitted.

Also in this Example 4, the effect similar to that of Example 3 can be obtained. Representation of graph of the experimental result will be omitted.

By the screening method described above, it is possible to screen the influence and toxicity of a cytotoxic factor (radiation, ultraviolet rays, drug and so on), protective ability to a cytotoxic factor, and susceptibility to a cytotoxic factor.

Example 5

Next, as Example 5, an example of detecting a difference in sensitivity between individuals will be described. In this example, a difference in sensitivity of thymocytes to radiation between WMN/Nrs strain rat, and F1 strain mice of C57BL/6 and C3H/He was examined. Also by using female and male mice of each strain, a difference between female and male in sensitivity of thymocytes to radiation was examined.

After purifying and isolating thymocytes sampled from each individual, the thymocytes were irradiated with 10 Gy X-ray, and the behavior of occurrence of apoptosis in variable incubation time was measured by FACSCALIBUR™ (a flow cytometry system). The protocol of this treatment is the same as that in Step 1 to Step 4 of Example 1.

Figure 6:
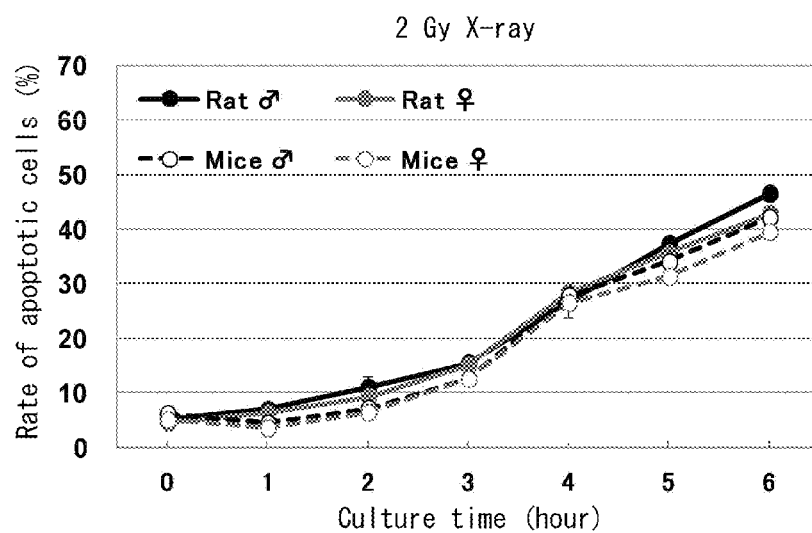
FIGS. 6(A) and 6(B) are explanatory diagrams for sensitivity to influence of radiation between different animal strains or different sexes of individuals according to cell size measurement graphs.
Figure 6:
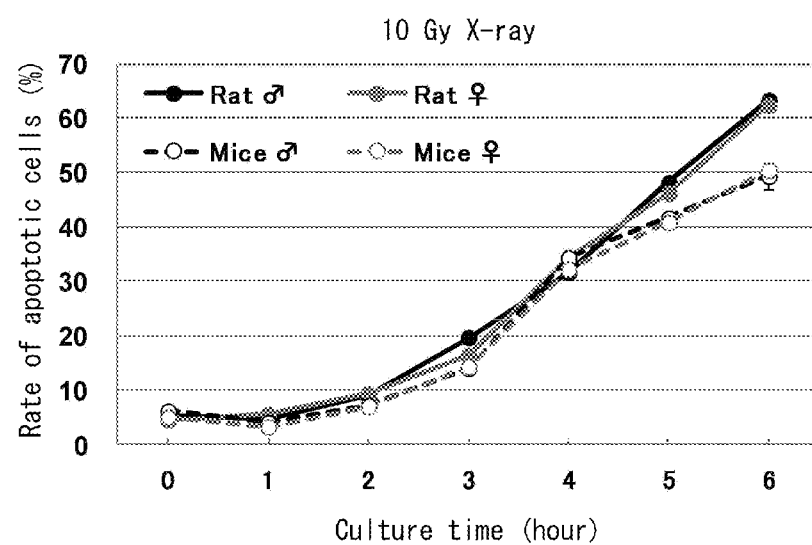

FIG. 6(A) and FIG. 6(B) respectively show charts for comparatively examining four groups: male and female WMN/Nrs strain rats, and male and female F1 strain mice. FIG. 6(A) shows measurement results in the cases of irradiation with 2 Gy X-ray, and FIG. 6(B) shows measurement results in the cases of irradiation with 10 Gy X-ray. In every case, the horizontal axis represents the incubation time, and the vertical axis represents the rate of the number of apoptotic cells to the entire number of cells.

The results demonstrate that in the strains used herein, there is no difference in sensitivity to radiation between female and male of the same strain (species) in radiation with 2 and 10 Gy of X-ray. On the other hand, a difference in sensitivity to radiation was observed between different species such as between rat and mouse. In particular, as shown in FIG. 6(B), a difference is remarkably shown at 6 hours of incubation after irradiation with 10 Gy X-ray, and it can be recognized that sensitivity to radiation is higher in WMN/Nrs strain rat than in F1 strain mouse.

Further, the rate of apoptotic cells increasing with the dose demonstrates the radiation-dose-dependent induction of apoptosis in thymocytes. Also, the rate of apoptotic cells increasing with the culture time demonstrates the culture-time-dependent induction of apoptosis in thymocytes.

Since the apoptotic cells starts increasing from about 2 hours of incubation time, the incubation time is preferably at least 2 hours or longer.

While not shown in the data, cell expansion also occurs as the incubation time exceeds 6 hours, and the inclination of the graph becomes gentle. For this reason, the incubation time is preferably within 6 hours rather than exceeding 6 hours.

While inclination of the graph of the rate of apoptotic cells to the incubation time increases with the time, the inclination becomes gentle after a lapse of 4 hours. This indicates that a phenomenon such as overkilling occurs after a lapse of 4 hours. Therefore, the most preferred incubation time is about 4 hours.

In the manner as described in Example 5, it is possible to detect the difference in sensitivity between individuals. Conventionally, a method of observing chromosome or the like has been employed to estimate the sensitivity to a cytotoxic factor (radiation, ultraviolet rays, drug or the like) or the degree of injury of an individual. In contrast, the present screening method can make it possible to objectively and economically estimate the sensitivity to a cytotoxic factor or the degree of injury of an individual (or individual person) in a short period of time. Also, by using lymphoid cells (leucocytes, lymphocytes or the like) that can be sampled from a living body, it is possible to detect the difference in sensitivity while keeping an individual alive.

For example, plural kinds of drugs are individually administered to a plurality of lymphoid cells sampled from a certain individual, and condensation of cell size may be measured for respective systems obtained by this administration. In this case, by comparing the measurement results of these systems, it is possible to estimate to which of the drugs the individual has high sensitivity. When measurement is performed in a plurality of systems in which administration amount of a drug to lymphoid cells is varied, it is also possible to estimate an appropriate administration amount.

Also, by performing such estimation, the present screening method can also be utilized for estimating a drug administration amount or estimating a radiation exposure dose.

In Examples 2 and 3, observation was performed after irradiating a living rat with radiation, however, a similar effect can be obtained when a living body is administered or irradiated with a cytotoxic factor, apart from radiation, and then lymphoid cells are sampled.

As described above, since the present screening method can make measurement easily in a short period of time with high accuracy, it can be an alternative technique for conventional techniques. The present screening method can be a method having high applicability for realizing custom-made medical treatments in future.

Further, since measurement can be performed by using a flow cytometry, a cell counter, a hematocyte measurement device and so on that are basic apparatuses possessed by general universities, research facilities, medical sites and so on, the present screening method can be used in many fields at low cost.

Also, the present screening method can perform a study by using lymphoid cells of a recombinant animal such as a knockout mouse in which one or more genes are vitiated by a gene knockout technique. Also in this case, it is possible to perform rapid, convenient and accurate screening.

Also, the present screening method can be applied as a rapid and convenient method in determination of toxicity of a new drug or the like in the Ministry of Health, Labour and Welfare, the Ministry of Agriculture, Forestry and Fisheries, enterprises and so on because it has an aspect of determining toxicity of a drug.

Example 6

Next, a screening kit that facilitates the aforementioned screening method will be described. The screening kit can be used for screening of toxicity of radiation and a drug, screening of a radiation-protecting agent, an antioxidant, and a radiation-sensitizing agent, screening of sensitivity to radiation or a drug of an individual and so on.

Figure 7:
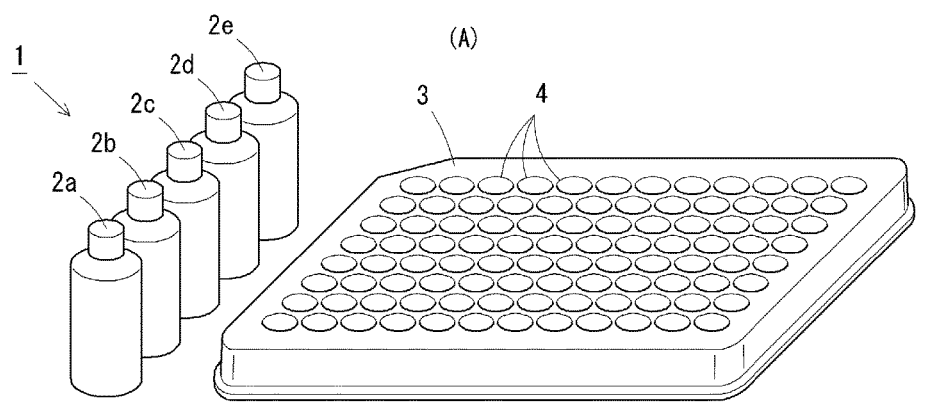
FIG. 7 is an explanatory diagram for a configuration of a screening kit.
Figure 7:
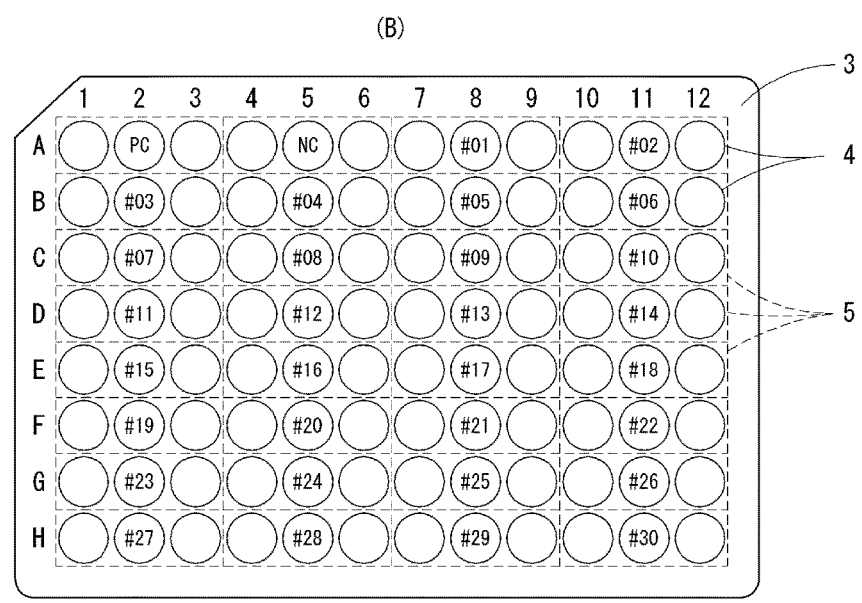

FIG. 7 is an explanatory view of a screening kit 1. FIG. 7(A) is a perspective view showing outer appearance and configuration of the screening kit 1, and FIG. 7(B) is a plan view of a 96-well plate 3 contained in the screening kit 1.

As shown in FIG. 7(A), the screening kit 1 has a positive control regent 2a, a negative control regent 2b, a protective ability control reagent 2c, a fluorescence staining solution 2d, a fixative solution 3e, and the 96-well plate 3.

The positive control regent 2a is, for example, a hydrogen peroxide solution ($H_2O_2$), a cytotoxic reagent (anticancer agent such as camptothecin (CPT) or fluorouracil (5-FU)), or a reagent that induces apoptosis in lymphoid cells.

The negative control regent 2b is a reagent that will not induce apoptosis in lymphoid cells, such as water, ethanol, and DMSO (dimethyl sulfoxide). Among these, the negative control regent 2b is a solution that dissolves a candidate drug, and is preferably used both for dissolving a candidate drug and as a negative control.

The protective ability control reagent 2c is a regent that protects from induction of apoptosis by the positive control regent 2a.

For example, in the case of screening oxidation stress, the positive control regent 2a may be a hydrogen peroxide solution, the negative control regent 2b may be a solvent for use in diluting a reagent, and the protective ability control reagent 2c may be vitamins (such as vitamin E). In the case of screening drug toxicity, the positive control regent 2a that induces apoptosis may be camptothecin, the negative control regent 2b may be a solvent for use in diluting a reagent, and the protective ability control reagent 2c may be a reagent that inhibits apoptosis (such as protease inhibitor functioning as an apoptosis inhibitor).

The fluorescence staining solution 2d is a reagent that fluorescently stains whole cells, cell membrane or nuclei, and is one or more of DAPI (4',6-diamidino-2-phenylindole), hoechst, fluorescein and so on.

In the case of staining lymphoid cells with the fluorescence staining solution 2d, it is possible to perform detailed observation, such as observation of not only the cell size but also the change in the shape, for example, by observing chromatin aggregation under a microscope.

Also, when blood is used as lymphoid cells, by performing the manipulation such as staining with a leucocyte-specific fluorescence staining solution 2d, staining with a lymphocyte-specific fluorescence staining solution 2d, or distinguishably staining leucocytes and lymphocytes with two different fluorescence staining solutions 2d having different fluorescent colors prior to measurement after incubation, it is possible to select specific cells (lymphocytes, leucocytes, erythrocytes, platelets, granulocytes (neutrophils, eosinophils, basophils), monocytes and so on) contained in the blood, and to measure condensation of the selected specific cells.

The fixative solution 2e is a cell fixative solution such as paraformaldehyde, formalin, and a cross linker which is a cross-linking agent. By performing a fixation treatment after the treatment (incubation) by using the fixative solution 2e, it becomes possible to store the treated cells, and to observe them some other time by fluorescence staining or the like.

The screening kit 1 may not contain the fluorescence staining solution 2d or/and the fixative solution 2e. Also in this case, screening can be performed by measuring the cell size of thymocytes, leucocytes, lymphocytes and so on.

The 96-well plate 3 has a plurality of wells 4 for accommodating a reagent. The well 4 has a bottomed cylindrical shape with open top. The 96-well plate 3 of this example includes a total of 96 (8×12) wells 4 arranged laterally.

As shown by a dotted line 5 of FIG. 7(B), well sets each consisting of three wells 4 can be used. In this case, for example, wells 4 of No. 1 to No. 3 on the A line are charged with the positive control regent 2a (PC), wells 4 of No. 4 to No. 6 on the A line are charged with the negative control regent 2b (NC), and in the same manner, section #01 to section #30 each consisting of a set of three wells 4 can be respectively charged with 30 reagents. Accordingly, it is possible to screen 30 reagents at a time, and to check each reagent in three wells 4.

Not limited to the above configuration, the 96-well plate 3 can be used in various ways. For example, section #01 may be charged with the protective ability control reagent 2c. Also, regarding each control reagent (2a, 2b, 2c), it may be changed in plural sections (using three wells 4 for one section) at different concentrations. In this case, a difference in influence depending on the difference in concentration can be measured.

By using a system that measure 96 samples automatically and sequentially (equipped with the function of keeping at low temperature and shaking regularly) in making measurement by a measurement device, a flow cytometry using the screening kit 1 as described above, it is possible to make the present screening method into an automatic assay having higher throughput. In other words, the effect identical to Step 4 of Example 1 to Example 4 can be obtained in a shorter time in a larger scale.

While the 96-well plate is used in this example, any appropriate plate such as a 48-well plate may be used without limited to this.

Also, future improvement in the technique of storing cells without injuring the cell would make it possible to include lymphoid cells that are subjected to freeze storage in liquid nitrogen in the screening kit 1. In such a case, the user can omit the step of preparing lymphoid cells, and use the kit more conveniently.

Also the screening kit 1 may include one or more of a lymphocyte isolation kit, a leucocyte isolation kit, a hemolytic agent, and beads having the same size as the cell size of a normal cell and/or cell size after condensation by apoptosis.

Accordingly, it is possible to use the kit more conveniently. When the lymphocyte isolation kit or the leucocyte isolation kit is packaged, isolation of lymphocytes or leucocytes can be facilitated.

When beads (that are fluorescent and distinguishable from cells) are packaged, it is possible to measure the size of a target cell by measuring cell size that is equivalent to the bead size, or by measuring cell size that is about half of the bead size. The beads used herein may be beads of the same size as a normal cell, beads of the same size as a cell condensed by apoptosis, or both of these.

Example 7

Next, a flow cytometer 10 which is a cell measurement device, and an analysis program 44 used for the flow cytometer 10 will be described. The flow cytometer 10 can be used for measurement in Example 1 to Example 5 described above, and is able to use the screening kit 1 of Example 6.

Figure 8:
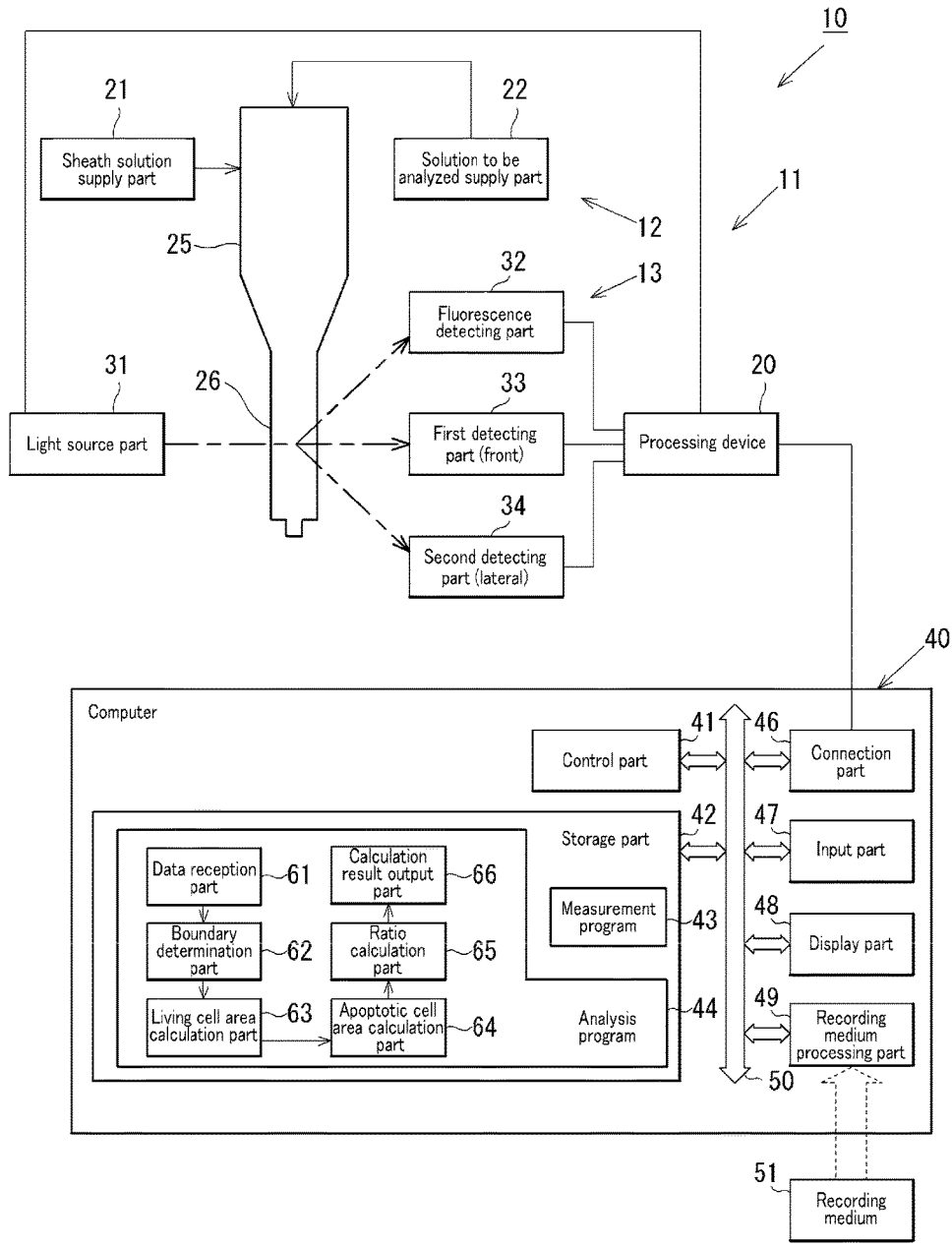
FIG. 8 is a block diagram showing a configuration of a flow cytometer.

FIG. 8 is a block diagram of the flow cytometer 10.

The flow cytometer 10 has a measurement device 11 and a computer 40.

The measurement device 11 has a fluid processing mechanism 12, an optical processing mechanism 13, and a processing device 20 for control-processing these mechanisms.

The fluid processing mechanism 12 has a sheath solution supply part 21, a solution to be analyzed supply part 22, a flow chamber 25, and a flow cell 26.

The sheath solution supply part 21 stores a sheath solution, and supplies the flow cell 26 with the sheath solution.

The solution to be analyzed supply part 22 supplies the flow chamber 25 with a solution to be analyzed. The solution to be analyzed is a solution containing lymphoid cells subjected to the treatments in Step 1 to Step 3 as described in Example 1 to Example 5, or a solution containing lymphoid cells subjected to the treatment with the positive control regent 2a or the negative control regent 2b described in Example 6.

The flow chamber 25 is substantially cylindrical, and has the flow cell 26 in its lower part. Inside the flow chamber 25, sheath flow (laminar flow) is formed in such a manner that the sheath solution supplied from the sheath solution supply part 21 surrounds the solution to be analyzed supplied from the solution to be analyzed supply part 22 in a cylindrical manner. Inside the flow chamber 25, cell particles of lymphoid cells contained in the solution to be analyzed are aligned, and the cell particles pass through one at a time through the flow cell 25.

The optical processing mechanism 13 has a light source part 31, a fluorescence detecting part 32, a first detecting part 33, and a second detecting part 34.

The light source part 31 continuously irradiates the cell particles aligned in the flow cell 25 with a laser beam.

The fluorescence detecting part 32 detects the light emitted from a fluorescently stained cell particle in response to the laser beam.

The first detecting part 33 detects front scattered light (scattered light in the traveling direction of the laser beam) generated from a cell particle in response to the laser beam.

The second detecting part 34 detects lateral scattered light (scattered light in the direction perpendicular to the traveling direction of the laser beam) generated from a cell particle in response to the laser beam.

The signals detected in the fluorescence detecting part 32, the first detecting part 33, and the second detecting part 34 are transmitted to the processing device 20. The processing device 20 performs signal processing on a received signal to convert an analog signal to digital data, and transmits the data to the computer 40.

The computer 40 includes a control part 41 composed of a CPU, a ROM and a RAM, for executing various manipulation processes and control processes, a storage part 42 such as a hard disc for storing various programs and data, a connection part 46 adapted to be connected with other devices such as the flow cytometer 10 via USB or the like to perform data communication, an input part 47 composed of a mouse, a keyboard and the like, for receiving input, a display part 48 composed of a liquid crystal display, CRT or the like, for displaying characters and images, and a recording medium processing part 49 for performing reading and writing of data with a recording medium 51 such as CD-ROM, and these pasts are connected via a system bus 50.

The recording medium 51 stores a measurement program 43 and an analysis program 44. The measurement program 43 and the analysis program 44 may be stored in the storage part 42 in such a manner that the programs are stored in the recording medium 51, and are installed in the computer 40.

The measurement program 43 is a program that executes measurement based on data received from the processing device 20 of the flow cytometer 10. The measurement program 43 is an existent program (for example, CellQuest Pro Software, from Becton, Dickinson and Company (BD)) installed in a flow cytometry or the like, and performs appropriate measurement such as measurement of cell size, counting of cell number of each cell size, and so on.

The analysis program 44 is a program for screening based on condensation of lymphoid cells as described in Example 1 to Example 5. The analysis program 44 has a data reception part 61, a boundary determination part 62, a living cell area calculation part (living cell calculation part) 63, an apoptotic cell area calculation part (apoptotic cell calculation part) 64, a ratio calculation part 65, and a calculation result output part 66.

Figure 9:
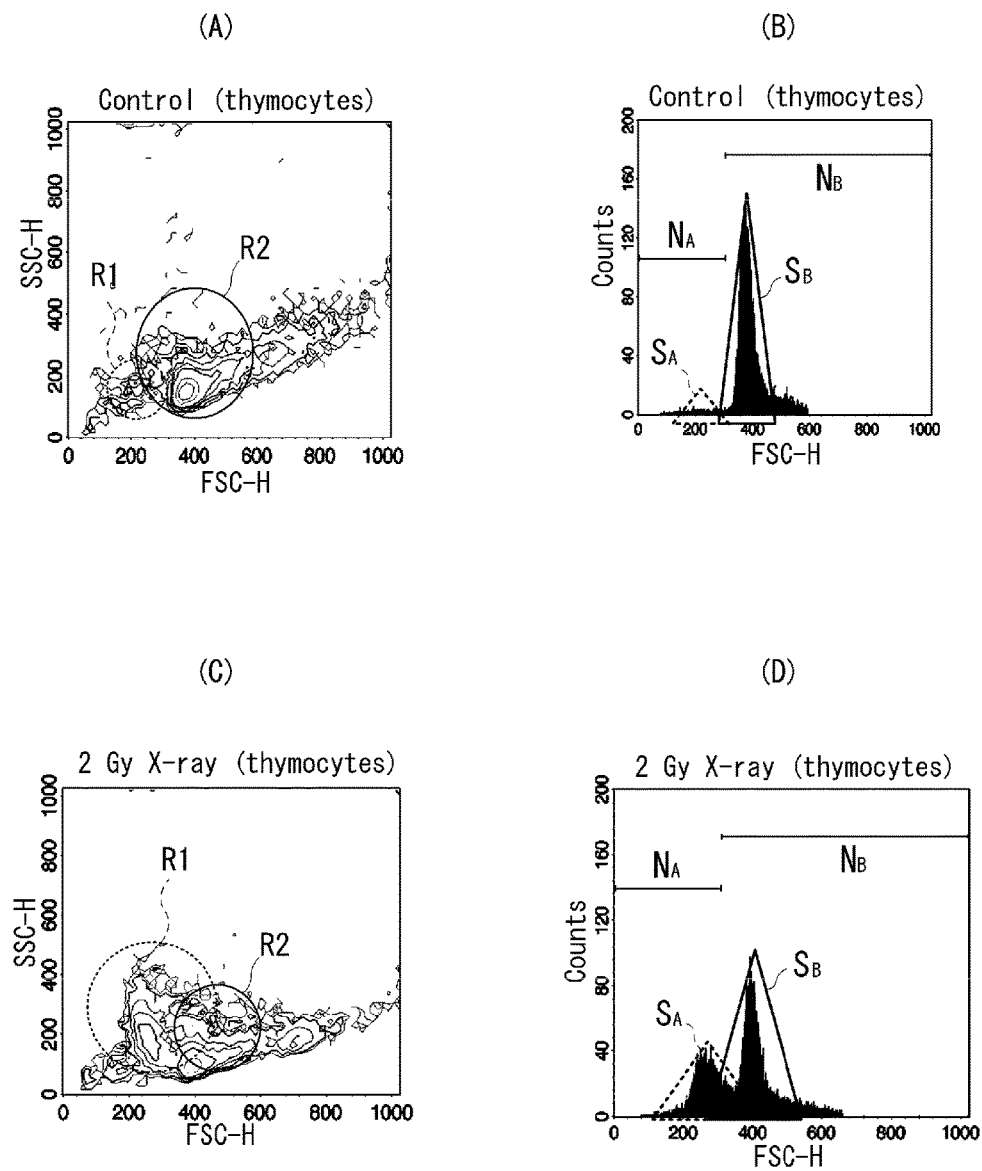
FIGS. 9(A) to 9(D) are explanatory diagrams for the principle of an analysis program according to cell size measurement graphs.

FIG. 9 is an explanatory diagram for explaining an analysis method by the analysis program 44. FIG. 9(A) and FIG. 9(B) show the measurement results of cell size of untreated thymocytes. Both of these are graphs showing cell size and count number, and a difference in appearance owes to the difference in the manner of representation. The sample of untreated lymphoid cells (control) means a sample under completely the same conditions as the sample to be comparatively examined, except for addition of a drug or radiation. Region R1 and area $S_A$ in the figure represents the region and area of the apoptotic cells, and region R2 and area $S_B$ in the figure represents the region and area of living cells. Herein, the area reflects the number of cells.

FIG. 9(C) and FIG. 9(D) show the measurement results of cell size of thymocytes irradiated with 2 Gy X-ray. Region R1 of apoptotic cells expands and area $S_A$ increases and region R2 of living cells reduces and area $S_B$ decreases after irradiation with 2 Gy X-ray in comparison with the control. Here, the area reflects the number of cells.

Referring to FIG. 9, manipulation of the analysis program 44 (see FIG. 8) will be described.

The data reception part 61 performs the step of receiving measurement data from the measurement program 43.

The boundary determination part 62 performs the step of determining cell size which forms a boundary between an apoptotic cell and a living cell for the received data. This calculation is made by determining the cross section point between the ridge line declining from the peak of the living cell and the ridge line declining from the peak of the apoptotic cell as shown in FIG. 9(B) and FIG. 9(D). In this calculation process, determination is made by appropriate methods including, for example, determining by using measurement data of the control, determining by using measurement data after treatment (measurement data of 2 Gy X-ray), or setting in advance.

The living cell area calculation part 63 performs the step of calculating the integral value of area $S_A$ formed by the cells smaller than the boundary determined in the boundary determination part 62.

The apoptotic cell area calculation part 64 performs the step of calculating the integral value of area $S_B$ formed by the cells larger than the boundary determined in the boundary determination part 62.

The ratio calculation part 65 performs the step of calculating the ratio between area $S_A$ and area $S_B$. This calculation is made according to [Mathematical formula 1] below.

$$\text{Rate of apoptotic cell (\%)} = \text{Area } S_A / \text{Area } S_A + \text{Area } S_B \times 100 \quad \text{[Mathematical formula 1]}$$

The calculation result output part 66 performs the step of outputting the calculation result to the display part 48 or the like. This calculation result can be appropriate results, including a value calculated by [Mathematical formula 1] above, and the effect of the reagent determined by the value. The output of the calculation result may be a calculation result for one reagent, or may be of an appropriate format such as a list format for 30 reagents in screening 30 reagents by using the screening kit 1 shown in Example 7. If the connection part 46 is connected with a printing device, the calculation result output part 66 can also print out the calculation result.

The flow cytometer 10 has a function of measuring samples while automatically taking out 96 samples sequentially from the 96-well plate, a function of keeping the sample at a predetermined temperature (for example, low temperature), and a function of shaking the sample regularly. Therefore, it is possible to perform automatic processing by using the screening kit 1 of Example 6.

By the foregoing flow cytometer 10, it is possible to perform screening of a radiation-protecting agent, an anti-oxidant, and a radiation-sensitizing agent, screening of toxicity of a drug, and screening of effect of a drug efficiently. The analysis program 44 can be used by being installed in the flow cytometer 10 such as an existent flow cytometry. Therefore, by installing the analysis program 44 into an existent device possessed by general universities, research facilities, medical sites and so on, from the recording medium 51, screening with high throughput becomes possible.

The present invention is not limited to the constitutions of the aforementioned embodiments, but many embodiments can be considered.

For example, it can be applied to other cells that will condense by apoptosis without limited to lymphoid cells. The other cells may be cells of a living body, preferably cells of a mammal, and may be cells differentiated by induction from ES cells or iPS cells. In this case, the cells that can be used in the screening method are cells that will condense without forming an apoptotic body generated by fragmentation of the cell.

As the object to be screened, a substance that induces apoptosis of cell, or a substance that protects cells from apoptosis by administration can be used.

Therefore, in application of the present screening method, it may be used for screening a drug for a disease associated with apoptosis. Examples of such a disease include cytopenia, inflammatory disease, autoimmune disease, destructive osteopathy, proliferative disorder, infectious disease, degenerative disease, apoptosis-associated disease, disease caused by excessive intake of alcohol at meals, virus-mediated disease, uveitis, inflammatory peritonitis, osteoarthritis, pancreatitis, asthma, adult type respiratory distress syndrome, glomerulonephritis, chronic rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scaur, graft-versus-host disease, organ transplantation rejection, osteoporosis, leukemia and related disorders, myelodysplastic syndrome, multiple myeloma-related disorder, acute myelocytic leukemia, chronic myelogenous leukemia, metastatic melanoma, Kaposi sarcoma, multiple myeloma, hemorrhagic shock, sepsis, septic shock, burn, shigellosis, Alzheimer's disease, Parkinson's disease, Huntington's disease, prion disease, cerebral ischemia, epilepsy, myocardial ischemia, acute or chronic cardiac disease, myocardial infarction, congestive heart failure, arteriosclerosis, coronary artery bypass grafting, spinal muscular atrophy, amyotrophic lateral sclerosis, multiple sclerosis, HIV-related encephalitis, aging, loss of hair, neurological injury caused by stroke, ulcerative colitis, traumatic brain injury, spinal cord injury, hepatitis A, hepatitis B, hepatitis C, hepatitis D, hepatitis E, hepatitis G, viral hepatitis of other type, liver disease induced by a drug (for example, paracetamol), yellow fever, dengue fever, Japanese encephalitis, liver disease, alcoholic hepatitis, renal disease, multiple cystic kidney disease, *Helicobacter pylori*-related gastroduodenal ulcer disease, HIV infection, tuberculosis, and meningitis.

Also in such an application, it is possible to perform objective and economical screening in a short period of time by measuring cell size.

INDUSTRIAL APPLICABILITY

The present invention is applicable to screening of toxicity of radiation and drug, screening of a radiation-protecting agent, screening of an antioxidant, screening of a radiation-sensitizing agent, screening of individual sensitivity to radiation or a drug, estimation of drug dosage, and estimation of individual exposure dose.

DESCRIPTION OF REFERENCE SIGNS

1: screening kit
2a: positive control regent
2b: negative control regent
3: 96-well plate
40: computer
44: analysis program
63: living cell area calculation part
64: apoptotic cell area calculation part
65: ratio calculation part
66: calculation result output part

The invention claimed is:

1. A screening method, comprising steps of:
   treating lymphoid cells consisting of preliminarily isolated lymphoid cells in culture medium at a temperature in a range from 3° C. to 26° C., with a cytotoxic factor by administering the cytotoxic factor to the lymphoid cells or irradiating the lymphoid cells with the cytotoxic factor;
   thereafter incubating the lymphoid cells treated with the cytotoxic factor for a selected time;
   measuring after the incubation, a cell size of both living cells and apoptotic cells of the treated lymphoid cells; and
   determining an influence of the cytotoxic factor on the lymphoid cells by change in the cell size of the lymphoid cells that have been treated with the cytotoxic factor, with at least one basis selected from the group consisting of (i) presence or absence of shifting of peak part of a cell size distribution, (ii) presence or absence and a degree of a change in a distribution area of the cell size, and (iii) presence or absence and a degree of a change in a cell number of the lymphoid cells having an original size, where the cell size is a size of a whole lymphoid cell, or a size of nucleus of a lymphoid cell, or both,
   wherein in the incubating step, the lymphoid cells are incubated in a culture medium supplemented with serum,
   the influence of the cytotoxic factor is at least one property thereof selected from the group consisting of toxicity, an effect of a drug, and sensitivity of a specific individual mammal from which or from whom the lymphoid cells are derived,
   the lymphoid cells that are influenced with the cytotoxic factor reduce the cell size thereof due to condensation, without forming an apoptotic body generated by fragmentation of the lymphoid cells and without changing a number of the lymphoid cells, and
   a total process comprising the treating of the lymphoid cells, the incubation of the treated lymphoid cells, and the measuring after the incubation, is completed within a period in a range from 6 hours to 8 hours.

2. The screening method according to claim 1,
   wherein the cytotoxic factor is at least one factor selected from the group consisting of radiation, a radiation-protecting agent, an antioxidant, a radiation-sensitizing agent, a drug, and ultraviolet rays.

3. The screening method according to claim 1,
   wherein the culture medium used in the incubation is a culture medium in which the condensation reduces an area of the lymphoid cells to approximately 70% or less relative to an area of lymphoid cells that have not been treated with the cytotoxic factor.

4. The screening method according to claim 3,
   wherein the selected time for the incubation is in a range of 6 hours or less.

5. The screening method according to claim 1,
   wherein in the treating of the lymphoid cells, the cytotoxic factor is administered to or irradiated a plurality of samples of the lymphoid cells at amounts that vary among the samples,
   the amounts include at least an amount at which no influence of the cytotoxic factor on the lymphoid cells is expected and an amount at which the influence is expected, and
   an amount of the cytotoxic factor that causes the influence is determined.

6. The screening method according to claim 1,
   wherein in the treating of the lymphoid cells, a plurality of the cytotoxic factors are administered to the lymphoid cells separately, and sensitivity of the lymphoid cells to each of the plurality of the cytotoxic factors is determined.

7. The screening method according to claim 1,
wherein the culture medium used in the incubation is a culture medium in which the condensation reduces an area of the lymphoid cells to approximately 50% or less relative to an area of lymphoid cells that have not been treated with the cytotoxic factor.

\* \* \* \* \*